US007235695B2

(12) United States Patent
Frydman et al.

(10) Patent No.: US 7,235,695 B2
(45) Date of Patent: Jun. 26, 2007

(54) CYCLOALKYL SUBSTITUTED POLYAMINES FOR CANCER THERAPY AND METHODS OF SYNTHESIS THEREFOR

(76) Inventors: Benjamin Frydman, 821 N. Holt Cir., Madison, WI (US) 53179; Aldonia L. Valasinas, 821 N. Holt Cir., Madison, WI (US) 53179; Andrei V. Blokhin, 5770 Dawley Dr., Fitchburg, WI (US) 53711; Aparajita Sarkar, 7226 Colony Dr., Madison, WI (US) 53719; Hirak S. Basu, 7226 Colony Dr., Madison, WI (US) 53719; Venodhar K. Reddy, 410 August Dr., Madison, WI (US) 53719; Laurence J. Marton, 581 Military Way, Palo Alto, CA (US) 94306; Yu Wang, 7110 Gladstone Dr., Madison, WI (US) 53719

( * ) Notice: Subject to any disclaimer, the term of this patent is extended or adjusted under 35 U.S.C. 154(b) by 0 days.

(21) Appl. No.: 11/205,341

(22) Filed: Aug. 16, 2005

(65) Prior Publication Data
US 2006/0030735 A1     Feb. 9, 2006

Related U.S. Application Data

(63) Continuation of application No. 10/313,530, filed on Dec. 6, 2002, now Pat. No. 6,982,351.

(60) Provisional application No. 60/339,205, filed on Dec. 7, 2001.

(51) Int. Cl.
*C07C 209/24* (2006.01)
*C07C 209/28* (2006.01)
*C07C 211/17* (2006.01)

(52) U.S. Cl. .................... 564/468; 564/153; 564/445; 564/453; 564/454; 564/455; 564/457; 564/461

(58) Field of Classification Search .................. None
See application file for complete search history.

(56) References Cited

U.S. PATENT DOCUMENTS

| | | | |
|---|---|---|---|
| 3,008,993 A | 11/1961 | Lesslie et al. | |
| 3,397,223 A | 8/1968 | Payne | |
| 3,773,833 A | 11/1973 | Henrici et al. | |
| 4,035,174 A | 7/1977 | Grier et al. | |
| 4,092,432 A | 5/1978 | Björklund et al. | |
| 4,153,567 A | 5/1979 | Kluger et al. | |
| 4,491,651 A | 1/1985 | Naiman | |
| 4,537,601 A | 8/1985 | Naiman | |
| 4,590,288 A | 5/1986 | Klemann | |
| 4,642,344 A | 2/1987 | Hajek et al. | |
| 4,698,446 A | 10/1987 | Lai et al. | |
| 4,935,449 A | 6/1990 | Bey et al. | |
| 5,021,409 A | 6/1991 | Murrer et al. | |
| 5,021,571 A | 6/1991 | Mease et al. | |
| 5,217,964 A | 6/1993 | Edwards et al. | |
| 5,354,782 A | 10/1994 | Edwards et al. | |
| 5,374,658 A | 12/1994 | Lau | |
| 5,401,443 A | 3/1995 | Nagano et al. | |
| 5,413,719 A | 5/1995 | Sivakumar et al. | |
| 5,434,145 A | 7/1995 | Edwards et al. | |
| 5,498,522 A | 3/1996 | Porter | |
| 5,516,807 A | 5/1996 | Hupe et al. | |
| 5,541,230 A | 7/1996 | Basu et al. | |
| H1633 H | 2/1997 | Hiebert et al. | |
| 5,606,053 A | 2/1997 | Prashad et al. | |
| 5,607,574 A | 3/1997 | Hart | |
| 5,608,061 A | 3/1997 | Ciszewski et al. | |
| 5,608,086 A | 3/1997 | Hemmerle | |
| 5,612,478 A | 3/1997 | Xu et al. | |
| 5,646,188 A | 7/1997 | Gilad et al. | |
| 5,654,287 A | 8/1997 | Prakash et al. | |
| 5,672,202 A | 9/1997 | Stirling et al. | |
| 5,677,349 A | 10/1997 | Gilad et al. | |
| 5,677,350 A | 10/1997 | Frydman | |
| 5,681,837 A | 10/1997 | Bergeron | |
| 5,707,532 A | 1/1998 | Guerro et al. | |
| 5,744,453 A | 4/1998 | Mintz et al. | |
| 5,763,388 A | 6/1998 | Lightsey et al. | |
| 5,843,959 A | 12/1998 | Bergeron, Jr. | |
| 5,880,161 A | 3/1999 | Basu et al. | |
| 5,889,061 A | 3/1999 | Frydman et al. | |
| 5,962,533 A | 10/1999 | Bergeron, Jr. | |
| 6,100,430 A | 8/2000 | Yamamoto et al. | |
| 6,392,098 B1 | 5/2002 | Frydman et al. | |
| 6,982,351 B2 | 1/2006 | Frydman et al. | |
| 2003/0130356 A1 | 7/2003 | Frydman et al. | |
| 2003/0195377 A1 | 10/2003 | Frydman et al. | |

FOREIGN PATENT DOCUMENTS

| | | |
|---|---|---|
| DE | 1295826 B1 | 5/1969 |
| JP | 05-032902 A | 2/1993 |
| JP | 07-277964 A | 10/1995 |

(Continued)

OTHER PUBLICATIONS

Alfonso, I. et al. (1996). "Sequential Biocatalytic Resolution of (+)-*trans*-cyclohexane-1,2-diamine. Chemoenzymatic Synthesis of an Optically Active Polyamine," *Chem. Commun.* 21:24171-2472.

(Continued)

*Primary Examiner*—Brian Davis
(74) *Attorney, Agent, or Firm*—Morrison & Foerster LLP

(57) ABSTRACT

Conformationally restricted polyamine compounds useful in treatment of cancer and other diseases marked by abnormal cell proliferation are disclosed. Improved methods of synthesizing such compounds are also disclosed. In one method of the invention, a carbene-bearing or carbene equivalent-bearing compound is reacted with the double bond of an alkene compound to form a cyclopropyl ring as the first step in the synthesis.

26 Claims, 14 Drawing Sheets

FOREIGN PATENT DOCUMENTS

| | | | |
|---|---|---|---|
| JP | WO-99/21542 A3 | 5/1999 |
| WO | WO-95/18091 A1 | 7/1995 |
| WO | WO-96/22962 A1 | 8/1996 |
| WO | WO-96/40096 A1 | 12/1996 |
| WO | WO-97/02027 A1 | 1/1997 |
| WO | WO-97/31611 A1 | 9/1997 |
| WO | WO-98/17624 A1 | 4/1998 |
| WO | WO-98/32729 A1 | 7/1998 |
| WO | WO-99/21542 A2 | 5/1999 |
| WO | WO-99/54283 A1 | 10/1999 |
| WO | WO-00/66175 A2 | 11/2000 |
| WO | WO-00/66175 A3 | 11/2000 |
| WO | WO-00/66528 A2 | 11/2000 |
| WO | WO-00/66528 A3 | 11/2000 |
| WO | WO-00/66587 A2 | 11/2000 |
| WO | WO-00/66587 A3 | 11/2000 |
| WO | WO-03/033455 A1 | 4/2003 |
| WO | WO-03/050072 A1 | 6/2003 |

OTHER PUBLICATIONS

Ashton, W.T. et al. (1988). "Synthesis and Antiherpetic Activityt of (±)-9-[[(Z)-2-(Hydroxymethyl)cyclopropyl]methyl]guanine and Related Compounds," *J. Med. Chem.* 31(12):2304-2315.

Bachmann, S. et al. (2001). "Cis-Selective Asymmetric Cyclopropanation of Olefins Catalyzed by Five-Coordinate [RuCl(PNNP)]+ Complexes," *Organometallics* 20(10):2102-2108.

Bachrach, U. et al. (1971). "Antivirus Action of Acrolein, Glutaraldehyde and Oxidized Spermine," *J. Gen. Virol.* 13:415-422.

Bachrach, U. et al. (1971). "Inactivation of Myxoviruses by Oxidized Polyamines," *J. Gen. Virol.* 11:1-9.

Bachrach, U. et al. (1972). "Effect of Oxidized Spermine and Other Aldehydes on the Infectivity of Vaccinia Virus," *Appl. Microbiol.* 23(2):232-235.

Barluenga, et al. (2000). "Diastereoselective Intermolecular Cyclopropanation of Simple Alkenes by Fischer Alkenyl and Heteroaryl Carbon Complexes and Chromium: Scope and Limitations," *J. Am. Chem. Soc.* 122:8145-8154.

Basu, H.S. et al. (1990). "Effects of Variation in the Structure of Spermine on the Association with DNA and the Induction of DNA Conformational Changes," *Biochem. J.* 269(2):329-334.

Behe, M. et al. (1981). "Effects of Methylation on a Synthetic Polynucleotide: the B—Z Transition in Poly(dG-m$^5$dC)-Poly(dG-m$^5$dC)," *Proc. Natl. Acad. Sci. USA* 78 (3):1619-1623.

Berchtold, C.M. et al. (1998). "Inhibition of Cell Growth in CaCO2 Cells by Polyamine Analogue $N^1$, $N^{12}$-Bis(Ethyl)Spermine is Preceded by a Reduction in MYC Oncoprotein Levels," *Journal of Cellular Physiology* 174(3):380-386.

Bergeron, R.J. et al. (1994). "Antiproliferative Properties of Polyamine Analogues: A Structure-Activity Study," *J. Med. Chem.* 37:3464-3476.

Bernacki, R.J. et al. (1992). "Antitumor Activity of $N,N^1$-Bis(Ethyl)Spermine Homologues Against Human MALME-3 Melanoma Xenografts," *Cancer Research* 52:2424-2430.

Bloomfield, V.A. et al. (1981). "Interactions of Polyamines with Polynucleotides" Chapter 10 *In Polyamines in Biology and Medicine*, Morris, D.L. et al., eds. Marcell Dekker, Inc.: New York, 8:184-206.

Byers, T.L. et al. (1990). "Regulation of Polyamine Transport in Chinese Hamster Ovary Cells," *Journal of Cellular Physiology* 143:460-467.

Casero, R.A. et al. (1995). "Growth and Biochemical Effects of Unsymmetrically Substituted Polyamine Analogues in Human Lung Tumor Cells," *Cancer Chermother. Pharmacol.* 36:69-74.

Casero, R.A. et al. (2001). "Terminally Alkylated Polyamine Analogues as Chemotherapeutic Agents," *Journal of Medicinal Chemistry* 44(1):1-26.

Chang, B.K. et al. (1992). "Antitumor Effects of N-Alkylated Polyamine Analogues in Human Pancreatic Adenocarcinoma Models," *Cancer Chemother. Pharmacol.* 30:179-182.

Chang, B.K. et al. (1992). "Regulatory and Antiproliferative Effects of N-Alkylated Polyamine Analogues in Human and Hamster Pancreatic Adenocarcinoma Cell Lines," *Cancer Chemother. Pharmacol.* 30:183-188.

Chang, B.K. et al. (1993). "Effects of Diethyl Spermine Analogues in Human Bladder Cancer Cell Lines in Culture," *Journal of Urology* 150:1293-1297.

Davidson, N.E. et al. (1993). "Growth Inhibition of Hormone-Responsive and -Resistant Human Breast Cancer Cells in Culture by $N^1$, $N^{12}$-Bis(Ethyl)Spermine," *Cancer Research* 53:2071-2075.

Doyle, M.P. et al. (1993). "Tetrakis[(4S)-4-phenyloxazolidin-2-one]dirhodium(II) and Its Catalytic Applications for Metal Carbene Transformations," *Helv. Chim. Acta.* 76:2227-2235.

Fernandez, C.O. et al. (1994). "Interactions Between Polyamine Analogs with Antiproliferative Effects and tRNA: a $^{15}$N NMR Analysis," *Cell Mol. Biol.* 40(7): 933-944.

Feuerstein, B.G. et al. (1991). "Implications and Concepts of Polyamine-Nucleic Acid Interactions," *Journal of Cellular Biochemistry* 46:37-47.

Fischer, H.A. (1975). "Synthesis of 3H-spermine," *J. Labeled Compd.* 11(1):141-143.

Frydman, B. et al. (1999). "Polyamine-based Chemotherapy of Cancer," *Opin. Ther. Patents.* 9(8):1055-1068.

Frydman, L. et al. (1992). "Interactions Between Natural Polyamines and tRNA: an $^{15}$N NMR Analysis," *Proc. Natl. Acad. Sci. USA* 89:9186-9190.

Gosule, L.C. et al. (1978). "DNA Condensation with Polyamines I. Spectroscopic Studies," *J. Mol. Biol.* 121:311-326.

Goto, M. et al. (1969). "Stereochemical Studies of Metal Chelates. III. Preparation and Stereochemistry of Cobalt (III) Complexes with C-Substituted Triethylenetetramines at the Central Ethylenediamine Bridge," *Inorg. Chem.* 8(2):358-366.

Ha, H.C. et al. (1998). "Unsymmetrically Substituted Polyamine Analogue Induces Caspase-Independent Programmed Cell Death in Bcl-2-Overexpressing Cells," *Cancer Research* 58:2711-2714.

Hafner, E.W. et al. (1979). "Mutants of *Escherichia coli* that do not Contain 1,4-Diaminobutane (Putrescine) or Spermidine," *J. Biol. Chem.* 254(24):12419-12426.

Herr, H.W. et al. (1984). "Potentiation of Methylglyoxal-Bis-Guanthydrazone by Alpha-Difluoromethylornithine in Rat Prostate Cancer," *Cancer* 53(6):1294-1298.

Horoszewicz, J.S. et al. (1983). "LNCaP Model of Human Prostatic Carcinoma,"*Cancer Res.* 43:1809-1818.

Igarashi, K. et al. (1990). "Spermine-Like Functions of $N^1$, $N^{12}$-Bis(Ethyl)Spermine: Stimulation of Protein Synthesis and Cell Growth and Inhibition of Gastric Ulceration," *Biochemical and Biophysical Research Communications* 172(2):715-720.

International Search Report mailed Apr. 4, 2003 for PCT Application No. PCT/US02/39293, three pages.

Jain, S. et al. (1989). "Base Only Binding of Spermine in the Deep Groove of the A-DNA Octamer d(GTGTACAC)," *Biochemistry* 28(6):2360-2364.

Jänne, J. et al. (1978). "Polyamines in Rapid Growth and Cancer," *Biochimica et Biophysica Acta*, 473:241-293.

Jeffers, L. et al. (1997). "Effetcs of the Polyamine Analogues BE-4-4-4-4, BE-3-7-3, and BE-3-3-3 on the Proliferation of Three Prostate Cancer Cell Lines," *Cancer Chemother. Pharmacol.* 40:172-179.

Kobiro, K. et al., (1992) "Synthesis and Molecular Structures of Nickel (II) Alkyl-Substituted Cyclam Complexes," *Inorg. Chem.* 31(4):676-685.

Kramer, D. et al. (1995). "Stable Amplification of the S-Adenosylmethionine Decarboxylase Gene in Chinese Hamster Ovary Cells," *J. Biol. Chem.* 270(5):2124-2132.

Kramer, D.L. et al. (1993). "Regulation of Polyamine Transport by Polyamines and Polyamine Analogs," *Journal of Cellular Physiology* 155:399-407.

Kramer, D.L. et al. (1997). "Effects of Novel Spermine Analogues on Cell Cycle Progression and Apoptosis in MALME-3M Human Melanoma Cells," *Cancer Res.* 57:5521-5527.

Lovaas, E. (1997). "Antioxidative and Metal-Chelating Effects of Polyamines," *Advances in Pharmacology* 38:119-149.

Mamont, P.S. et al. (1978). "Anti-Proliferative Properties of DL-α-Difluoromethyl Ornithine in Cultured Cells. A Consequence of the Irreversible Inhibition of Ornithine Decarboxylase," *Biochem. Biophys. Res. Commun.* 81(1):58-66.

Marton, L.J. et al. (1995). "Polyamines as Targets for Therapeutic Intervention," *Ann. Rev. Pharm. Toxicol.* 35:55-91.

McCloskey, D.E. et al. (2000). "Effects of the Polyamine Analogues $N^1$-Ethyl-$N^{11}$-((cyclopropyl)methyl)-4,8-diazaundecane and $N^1$-Ethyl-$N^{11}$-((cycloheptyl)methyl)-4,8-diazaundecane in Human Prostate Cancer Cells," *Clinical Cancer Research* 6:17-23.

Mi, Z. et al. (1998). "Human Prostatic Carcinoma Cell Lines Display Altered Regulation of Polyamine Transport in Response to Polyamine Analogs and Inhibitors," *The Prostate* 34:51-60.

Morgan, D.M.L. et al. (1983). "Polyamine Oxidation and the Killing of Intracellular Parasites," *Adv. Polyamine Res.* 4:169-174.

Morgan, D.M.L. et al. (1986). "The Effect of Purified Aminoaldehydes Produced by Polyamine Oxidation on the Development in vitro of *Plasmodium falciparum* in Normal and Glucose-6-Phosphate-Dehydrogenase-Deficient Erythrocytes," *Biochem. J.* 236:97-101.

Morgan, D.M.L. (1998). "Polyamines. An Introduction" Chapter 1 *In Methods in Mol. Biology*, Morgan, D., ed., Humana Press Inc.: New Jersey, 79:3-30.

Nagarajan, S. et al. (1987). "Chemistry of Naturally Occurring Polyamines. 11. Unsaturated Spermidine and Spermine Derivatives," *J. Org. Chem.* 52(22):5044-5046.

Nguyen, S.T. et al. (1999). "Diastereo—And Enantioselective Cyclopropanation of Alkenes Catalyzed by Ruthenium-Schiff-Base Complexes," *Abstracts of Papers, Part 1, 218th ACS National Meeting*, New Orleans, LA Aug. 22-25, 1999, American Chemical Society: Washington, DC. Abstract No. INOR-104, one page.

Nishimura, K. et al. (1971). "Phagocidal Effects of Acrolein," *Biochim. Biophys. Acta* 247:153-156.

Payne, G.B. (1967). "Cyclopropanes from Reactions of Ethyl(Dimethylsulfuranylidene)acetate with α,β-Unsaturated Compounds," *Journal of Organic Chemistry* 32(11):3351-3355.

Pegg, A.E. et al. (1982). "Polyamine Metabolism and Function," *Am. J. Cell. Physiol.* 243(5):C212-C221.

Pohjanpelto, P. et al. (1981). "Polyamine Starvation Causes Disappearance of Actin Filaments and Microtubules in Polyamine-Auxotrophic CHO cells," *Nature* 293:475-477.

Porter, C.W. et al. (1987). "Relative Abilities of Bis(ethyl) Derivatives of Putrescine, Spermidine, and Spermine to Regulate Polyamine Biosynthesis and Inhibit L1210 Leukemia Cell Growth," *Cancer Res.* 47(11)2821-2825.

Porter, C.W. et al. (1988). "Enzyme Regulation as an Approach to Interference with Polyamine Biosynthesis-An Alternative to Enzyme Inhibition," *Advances in Enzyme Regulation* 27:57-79.

Porter, C.W. et al. (1988). "Regulation of Polyamine Biosynthetic Activity by Spermidine and Spermine Analogs-A Novel Antiproliferative Strategy," *Adv. Exp. Med. Biol.* 250:677-690.

Porter, C.W. et al. (1991). "Correlations Between Polyamine Analogue-induced Increases in Spermidine/Spermine $N^1$-Acetyltransferase Activity, Polyamine Pool Depletion, and Growth Inhibition in Human Melanoma Cell Lines," *Cancer Res.* 51:3715-3720.

Reddy, V.K. et al. (1998). "Conformationally Restricted Analogues of $^1$N, $^{12}$N-Bisethylspermine: Synthesis and Growth Inhibitory Effects on Human Tumor Cell Lines," *J. Med. Chem.* 41(24):4723-4732.

Reddy, V.K. et al. (2001), "Cis-Unsaturated Analogues of 3,8,13,18,23-Pentaazapentacosane (BE-4-4-4-4): Synthesis and Growth Inhibitory Effects on Human Prostate Cancer Cell Lines," *J. Med. Chem.* 44:404-417.

Redgate, E.S. et al. (1995). "Polyamines in Brain Tumor Therapy," *J. Neuro-Oncol.* 25:167-179.

Salaün, J. (1997). "Synthetic Potential and Bioactivity of Cyclopropanes," *Russian Journal of Organic Chemistry* 33(6):742-780.

Salaün, J. (2000). "Cyclopropane Derivatives and Their Diverse Biological Activities," *Topics in Current Chemistry* 207:1-67.

Salaün, J. et al. (1995). "Biologically Active Cyclopropanes and Cyclopropenes," *Current Medicinal Chemistry* 2:511-542.

Shappell, N.W. et al. (1992). "Differential Effects of the Spermine Analog, $N^1$, $N^{12}$-Bis(ethyl)-spermine, on Polyamine Metabolism and Cell Growth in Human Melanoma Cell Lines and Melanocytes," *Anticancer Research* 12:1083-1089.

Sharma, A. et al. (1997). "Antitumor Efficacy of $N^1$, $N^{11}$-Diethylnorspermine on a Human Bladder Tumor Xenograft in Nude Athymic Mice," *Clin. Cancer Res.* 3:1239-1244.

Snyder, R. D. et al. (1991). "Effects of Polyamine Analogs on the Extent and Fidelity of in vitro Polypeptide Synthesis," *Biochem. Biophys. Res. Commun.* 176(3):1383-1392.

Snyder, R.D. et al. (1994). "Anti-Mitochondrial Effects of Bisethyl Polyamines in Mammalian Cells," *Anticancer Res.* 14:347-356.

Valasinas, A. et al. (2001). "Conformationally Restricted Analogues of $^1$N, $^{14}$N-Bisethylhomospermine (BE-4-4-4): Synthesis and Growth Inhibitory Effects on Human Prostate Cancer Cells," *J. Med. Chem.* 44(3):390-403.

Webb, H.K. et al. (1999). "1-(N-Alkylamino)-11-(N-ethylamino)-4,8-diazaundercanes: Simple Synthetic Polyamine Analogues That Differentially Alter Tubulin Polymerization," *J. Med. Chem.* 42:1415-1421.

Wunz, T.P. et al. (1987). "New Antitumor Agents Containing the Anthracene Nucleus," *J. Med. Chem.* 30(8):1313-1321.

Yaun, Z-M. et al. (1994). "Cytotoxic Activity of $N^1$- and $N^8$-Aziridinyl Analogs of Spermidine," *Biochemical Pharmacology* 47(9):1587-1592.

Zagaja, G.P. et al. (1998). "Effects of Polyamine Analogues on Prostatic Adenocarcinoma Cells in vitro and in vivo," *Cancer Chem. Pharm.* 41(6):505-512.

Effects of SL-11232 in PC-3 cells after 5 days of incubation
(Only attached cells)

Effects of SL-11241 in PC-3 cells after 5 days of incubation

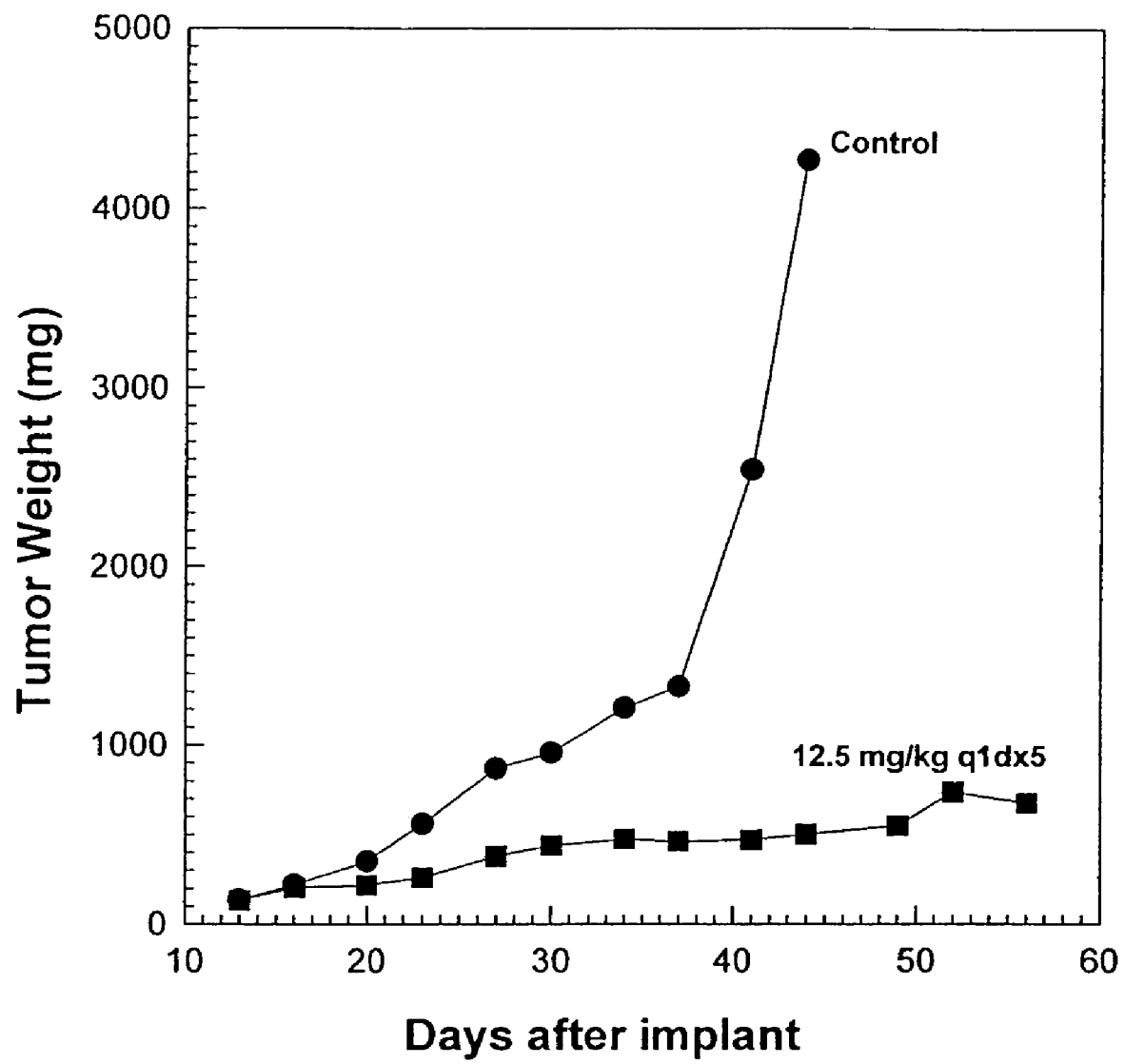

dose 12.5 mg/kg/inj IP Q1Dx5(SD) Rx 9-13, 23-27

CYCLOALKYL SUBSTITUTED POLYAMINES FOR CANCER THERAPY AND METHODS OF SYNTHESIS THEREFOR

CROSS-REFERENCE TO RELATED APPLICATIONS

This application is a continuation of U.S. patent application Ser. No. 10/313,530, filed Dec. 6, 2002, now U.S. Pat. No. 6,982,351, which claims the priority benefit of U.S. Provisional Patent Application No. 60/339,205 filed Dec. 7, 2001, now abandoned. The contents of those applications are hereby incorporated by reference herein in their entireties.

STATEMENT OF RIGHTS TO INVENTIONS MADE UNDER FEDERALLY SPONSORED RESEARCH

Not applicable.

TECHNICAL FIELD

This invention is directed to cycloalkyl-substituted polyamine analog compounds, particularly cyclopropyl-containing polyamine analog compounds, useful as chemotherapy treatments in cancer and other diseases caused by abnormal cell proliferation, as well as improved methods for synthesizing such compounds.

BACKGROUND OF THE INVENTION

While substantial progress has been made in prevention, detection, and treatment of certain forms of cancer, it remains one of the leading causes of death in the developed world. Certain forms of cancer, such as prostate cancer, have high 5-year survival rates when detected in the early stages, but much lower survival rates when detected after metastasis. There is thus a need for new and improved agents for treating cancer and other diseases marked by abnormal cell proliferation.

Polyamines are naturally-occurring compounds which are essential for the growth and division of cells. Polyamines (including putrescine, spermidine, and spermine) increase in proliferating issues. A number of polyamine analogues have shown promise as anticancer agents. They are able to kill cells and inhibit cell growth both in vitro and in vivo. Most successful among these analogues have been the α-N, ω-N alkyl derivatives of the higher and lower homologues of spermine, although several alkylated diamines also show promise as inhibitors of tumor cell proliferation. See, e.g., U.S. Pat. Nos. 5,541,230 and 5,880,161. Many hypotheses have been advanced to explain the biological effects of the polyamines; one of the most compelling hypotheses attributes their effects to polyamine binding to nucleic acids and to receptor targets. Since spermidine and spermine are strong bases, they are protonated at physiological pH and can therefore bind to the negatively charged nucleic acids either by electrostatic interactions or by hydrogen bonding.

Polyamines are known to interact with and induce structural changes in DNA in cell-free systems. Spermidine and spermine can cause DNA to condense and aggregate and can induce both B-to-Z and B-to-A transitions in certain DNA sequences. Molecular mechanics studies of spermine-DNA interactions have shown that, in a minimum energy conformation, spermine is bound in a cisoidal conformation that wraps around the major groove of the double helix. Spermine and its α-N, ω-N-bisethylated higher and lower homologues, as well as spermidine, have been shown to bind to t-RNA. Using $^1$H NMR analysis, spermine and $^1$N, $^{12}$N-bisethylspermine (BES) were found to bind at the TψC loop of t-RNA$^{Phe}$. The binding is not of an electrostatic nature, but rather a consequence of the different hydrogen-bonding modes that can be established between both types of molecules. Finally, polyamines have recently been shown to bind to receptors such as the N-methyl-D-glutamate (NMDA) receptor and the glutamate receptor (Glu-R) and to block and modulate a number of ion channels, results that open new vistas in the pharmacology of the polyamines.

DNA-interacting drugs have long been of interest as anticancer agents. Mechanical models of the DNA double helix have created an image of a rigid structure; however, experimental evidence suggests that DNA has considerable flexibility. When designing polyamine analogues that can bind to DNA, structural modifications considered include variations in the number of distance of carbons between nitrogens and/or terminal N-substitutions of different types. This invention is directed to the design and synthesis of chiral analogues of spermine and other naturally and non-naturally occurring polyamines that bind DNA, t-RNA, or other polyamine binding sites, in a modified and selective fashion due to their increased conformational rigidity. The introduction of restriction in the free rotation about the single bonds in a flexible molecule such as spermine (which has a myriad of potential conformations) can result in spatial rigidity which can introduce bends, kinks, or loops at their binding domains. The introduction of conformational restriction has been very fruitful in the design of peptidomimetics, and a recent report described the synthesis of chiral pyrrolidyl polyamines.

As a starting point, rigid analogues of spermine were constructed where the added atoms or bonds had minimal effect on the size and molecular weight of the parent compound. The simple addition of a cyclopropyl ring to the butane segment of spermine introduces chirality and conformational restriction in an otherwise flexible molecule.

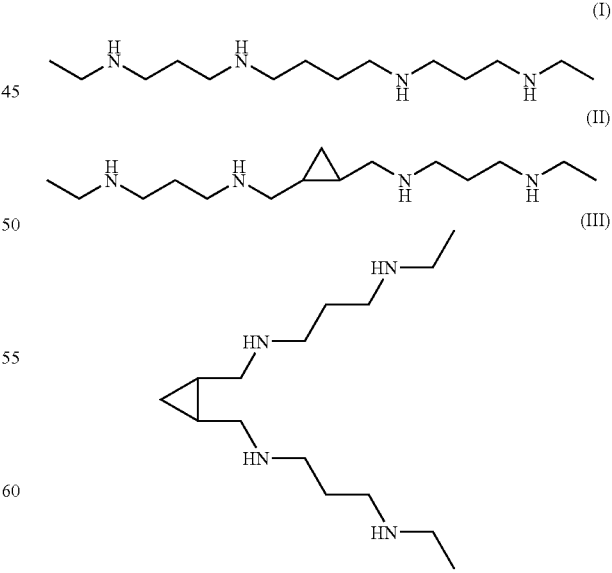

The structure (I) shows the conformation of $^1$N, $^{12}$N-bisethylspermine (BES), while the two structures (II) and (III) show the conformation of the trans-isomer (II) and cis-isomer (III) resulting from replacing the central butane segment in BES with trans- and cis-1,2-dimethylcyclopropyl residues, respectively.

Cyclopropane derivatives are also known to have important biological functions. Incorporating a cyclopropane moiety into a polyamine structure can enhance the anticancer effect of the polyamine analog via additional mechanisms complementary to the conformational effect on the polyamine analog.

The design of new and more efficacious tetramines offers several advantages. While the precise mechanisms by which polyamines kill tumor cells and cause systemic toxicity are still not entirely clear, it has been established that polyamines and their analogues bind to nucleic acids and alter their conformations, that they bind to receptor targets, that they drastically reduce the level of ornithine decarboxylase (the first enzyme in the pathway that leads to spermine biosynthesis in mammals), that they upregulate the levels of spermidine/spermine N-acetyltransferase (the enzyme involved in the catabolism and salvage pathways of spermine and spermidine), that they may inhibit the uptake of the natural polyamines by the cells, and that, as a result, they deplete endogenous polyamine pools needed for cell replication. Cell death can result from any one of these effects or from several of them acting in tandem. On the other hand, the main advantage in the design of new tetramines is that structure-activity studies (SARs) have shown that relatively small structural changes in the aliphatic skeletons of the polyamines can cause pronounced differences in their pharmacological behavior and toxic side effects as well as in their antineoplastic activities, both at the cellular level as well as in animal models.

It has been repeatedly shown that $^1N,^{14}N$-bisethylhomospermine (BE-4-4-4), a higher homologue of bisethylspermine, is a powerful cytotoxic drug but has a narrow therapeutic window. The results for animal trials reported against tumors such as L1210 leukemia or Lewis lung carcinoma grafted in athymic nude mice are indeed impressive; about a 6-fold increase in lifespan, as compared to control, was achieved. However, maximum tolerated dose (MTD) values for multiple injection (ip) schedules were found to be ca. 6 mg/kg, doses close to the levels necessary to achieve efficient antitumor activity in human tumor xenografts. It is therefore desirable to design compounds with a wider therapeutic window.

In pursuit of this goal, conformational restrictions were introduced into the BE-4-4-4 structure in order to increase its therapeutic activity, prompted by the promising results obtained with conformationally restricted analogues of bisethylspermine. Since the latter was found to be highly cytotoxic against a line of human prostate cancer cells, the new tetramines were assayed against several lines of human prostate cancer cells. LnCap, DU 145, DuPro, and PC-3. The results suggest that it is possible to markedly improve the therapeutic efficacy of BE-4-4-4-like compounds against human prostate cancer cells by introducing certain conformational restrictions.

Conformationally-restricted polyamine analogs and methods of synthesizing such analogs have been disclosed in U.S. Pat. Nos. 5,889,061 and 6,392,098 and International Patent Applications WO 98/17624 and WO 00/66587. In view of the utility of these compounds for treating neoplastic cell growth, additional synthetic methods are desirable, particularly synthetic methods amenable to large-scale synthesis. This invention provides improved methods for synthesizing cyclopropyl-containing polyamine analogs, as well as novel polyamine analogs containing cyclopropyl groups.

DISCLOSURE OF THE INVENTION

In its various embodiments, the invention embraces new methods for making polyamine analogs, as well as novel polyamine analogs (which can be made by the methods of the invention, or by any other synthetic method).

In one embodiment, the invention embraces a method for making a polyamine containing a cyclopropyl group by adding a carbene-bearing or carbene equivalent-bearing compound across a double bond of an alkene compound to form a cyclopropyl ring, where the carbene-bearing or carbene equivalent-bearing compound, or the alkene compound, or both have additional functional groups which can be reacted in further steps. Optionally, further chemical reactions can be performed on the additional functional groups incorporated into the cyclopropane ring from the carbene-bearing or carbene equivalent-bearing compound, or from the alkene compound, or on both. Amino-bearing groups can then be reacted with the additional functional groups which were incorporated into the cyclopropane ring from the carbene-bearing or carbene equivalent-bearing compound, or from the alkene compound, or from both. In one embodiment, the carbene-bearing or carbene equivalent-bearing compound is an ylide, such as a sulfur ylide. In further embodiments, the additional functional groups incorporated into the cyclopropane ring from the carbene-bearing or carbene equivalent-bearing compound, or from the alkene compound, or from both, include at least one carboxylic ester.

In one embodiment where the additional functional groups include at least one carboxylic ester, the carboxylic ester is on the carbene-bearing or carbene equivalent-bearing compound, and the formal negative charge of the carbene in the carbene-bearing or carbene equivalent-bearing compound is at the carbon in the alpha position to the carbonyl carbon of the carboxylic ester group. In other embodiments where the additional functional groups include at least one carboxylic ester, the carboxylic ester is on the alkene compound, and the double bond of the alkene compound is between the carbons in the alpha and beta positions to the carbonyl carbon of the carboxylic ester group. In yet further embodiments, the carbene-bearing or carbene equivalent-bearing compound has at least one carboxylic ester, the alkene compound has at least one carboxylic ester, and the step of optionally performing further chemical reactions is carried out on both the additional functional groups of the carbene-bearing or carbene equivalent-bearing compound and the alkene compound, and comprises the step of converting the carboxylic esters to free carboxylic acids. In another embodiment, further chemistry is performed to activate the carboxylic acids with a leaving group, such as by reaction with thionyl chloride to produce carboxylic acid chlorides.

In another embodiment, the step of reacting amino-bearing groups with the additional functional groups of the carbene-bearing or carbene equivalent-bearing compound, or the alkene compound, or both, is carried out on both the additional functional groups of the carbene-bearing or carbene equivalent-bearing compound and the alkene compound.

In yet other embodiments, the invention embraces methods of making a compound of the formula:

E-NH-B-A-B-NH-B-A-B-NH-B-A-B-NH(-B-A-B-NH)$_x$-E wherein A is independently selected from the group consisting of a single bond, $C_2$–$C_6$ alkyl, $C_2$–$C_6$ hydroxyalkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of a single bond, $C_1$–$C_6$ alkyl, $C_1$–$C_6$ hydroxyalkyl, and $C_2$–$C_6$ alkenyl; E is independently selected from the group consisting of H, $C_1$–$C_6$ alkyl, $C_1$–$C_6$ hydroxyalkyl, $C_2$–$C_6$ alkenyl, and $C_2$–$C_6$ alkynyl; and x is an integer from 0 to 16; with the proviso that at least one A moiety is cyclopropyl, and that each -B-A-B- subunit contains at least two carbon atoms; and all salts and stereoisomers thereof; comprising forming at least one of the cyclopropyl A moieties by the method described above. In other embodiments, x is an integer from 1 to 16. In additional embodiments, the molecule contains one, and only one, cyclopropyl moiety. In additional embodiments, the molecule contains one, and only one, cycloalkyl moiety, and that cycloalkyl moiety is a cyclopropyl moiety. In other embodiments, the compound to be synthesized by the methods of the invention is of the formula:

E-NH-B-A-B-NH-B-A-B-NH-B-A-B-NH-E.

In further embodiments, the compound is of the formula:

E-NH-B-A-B-NH-B-A-B-NH-B-A-B-NH-B-A-B-NH-E.

In yet further embodiments, the compound is of the formula:

E-NH-B-A-B-NH-B-A-B-NH-B-A-B-NH(-B-A-B-NH)$_x$-E wherein x is an integer between 2 and 16.

In yet further embodiments, for the compound to be synthesized above, E is selected from H, $C_1$–$C_2$ alkyl, and t-butyl; or E is —CH$_2$CH$_3$. In yet further embodiments, each -B-A-B- subunit which does not contain a cyclopropyl moiety is independently selected from $C_2$–$C_4$ alkyl; or —CH$_2$CH$_2$CH$_2$CH$_2$—; or —CH$_2$CH$_2$CH$_2$—; or is independently selected from —CH$_2$CH$_2$CH$_2$— and —CH$_2$CH$_2$CH$_2$CH$_2$—. In yet further embodiments, each -B-A-B- subunit which contains a cyclopropyl moiety is

in the E configuration; or each -B-A-B- subunit which contains a cyclopropyl moiety is

in the Z configuration; or each -B-A-B- subunit which contains a cyclopropyl moiety is independently selected from

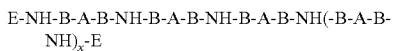

in the E or Z configuration.

The invention also embraces compositions of matter comprising a compound of the formula:

E-NH-B-A-B-NH-B-A-B-NH-B-A-B-NH(-B-A-B-NH)$_x$-E wherein A is independently selected from the group consisting of a single bond, $C_2$–$C_6$ alkyl, $C_2$–$C_6$ hydroxyalkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of a single bond, $C_1$–$C_6$ alkyl, $C_1$–$C_6$ hydroxyalkyl, and $C_2$–$C_6$ alkenyl; E is independently selected from the group consisting of H, $C_1$–$C_6$ alkyl, $C_1$–$C_6$ hydroxyalkyl, $C_2$–$C_6$ alkenyl, and $C_2$–$C_6$ alkynyl; and x is an integer from 0 to 16; with the proviso that at least one A moiety is cyclopropyl, and that each -B-A-B- subunit contains at least two carbon atoms; and all salts and stereoisomers thereof. In additional embodiments, x is an integer from 1 to 16. In additional embodiments, the molecule contains one, and only one, cyclopropyl moiety. In additional embodiments, the molecule contains one, and only one, cycloalkyl moiety, and that cycloalkyl moiety is a cyclopropyl moiety. In additional embodiments, the compound is of the formula:

E-NH-B-A-B-NH-B-A-B-NH-B-A-B-NH-B-A-B-NH-E.

In additional embodiments, the compound is of the formula:

E-NH-B-A-B-NH-B-A-B-NH-B-A-B-NH(-B-A-B-NH)$_x$-E wherein x is an integer between 2 and 16. In yet further embodiments of these compounds, E is selected from H, $C_1$–$C_2$ alkyl, and t-butyl, or E is —CH$_2$CH$_3$. In yet further embodiments of these compounds, each -B-A-B- subunit which does not contain a cyclopropyl moiety is independently selected from $C_2$–$C_4$ alkyl, or —CH$_2$CH$_2$CH$_2$CH$_2$—, or —CH$_2$CH$_2$CH$_2$—, or each -B-A-B- subunit which does not contain a cyclopropyl moiety is independently selected from —CH$_2$CH$_2$CH$_2$— and —CH$_2$CH$_2$CH$_2$CH$_2$—. In yet further embodiments, each -B-A-B- subunit which contains a cyclopropyl moiety is

in the E configuration; or each -B-A-B- subunit which contains a cyclopropyl moiety is

in the Z configuration; or each -B-A-B- subunit which contains a cyclopropyl moiety is independently selected from

in the E or Z configuration.

In another embodiment, the invention embraces a compound of the formula:

wherein the alkylamine substituents on the cyclopropyl ring are trans to each other, and all salts thereof.

BRIEF DESCRIPTION OF THE DRAWINGS

FIG. 8a is a graph depicting the effect of SL-11231 on DU-145 growth in xenograft. Circles indicate data for control, squares indicate data for SL-11231.

BEST MODE FOR CARRYING OUT THE INVENTION

Figure 1:
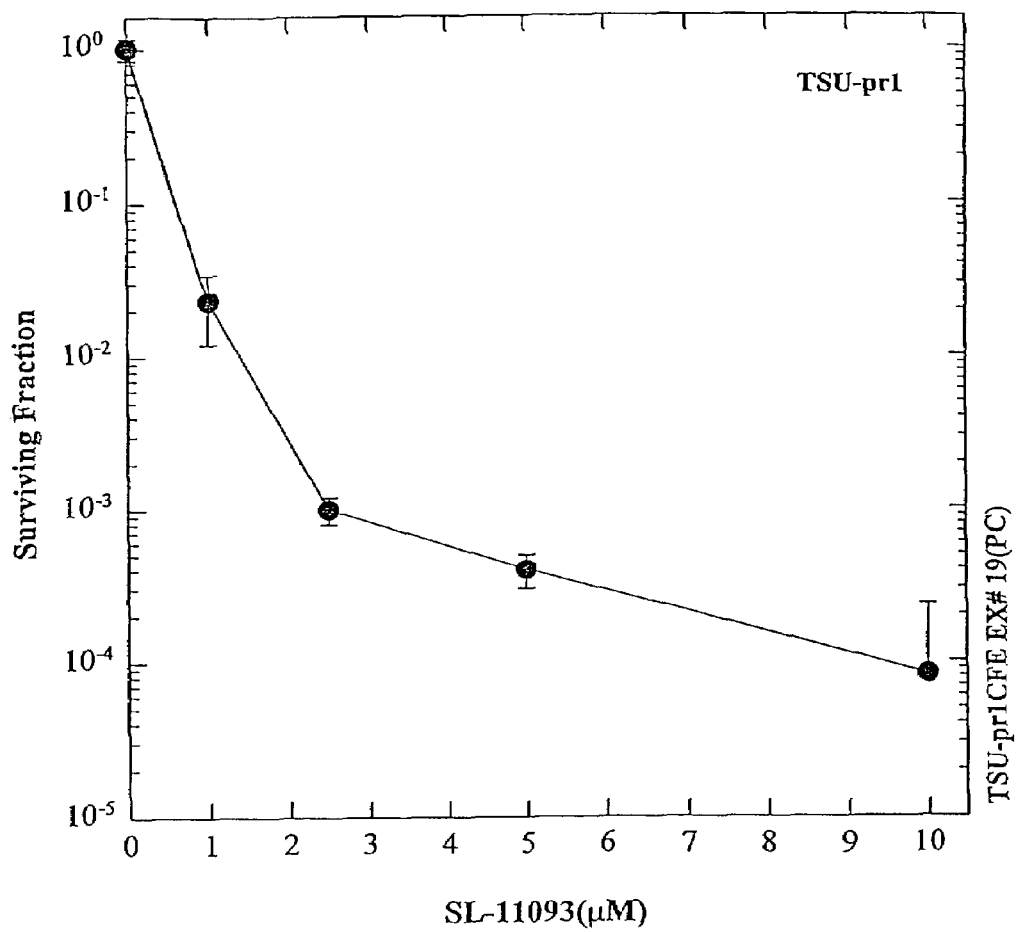
FIG. 1 is a graph depicting the effects of SL-11093 in TSU-pr1 cells after 5 days incubation.
Figure 2:
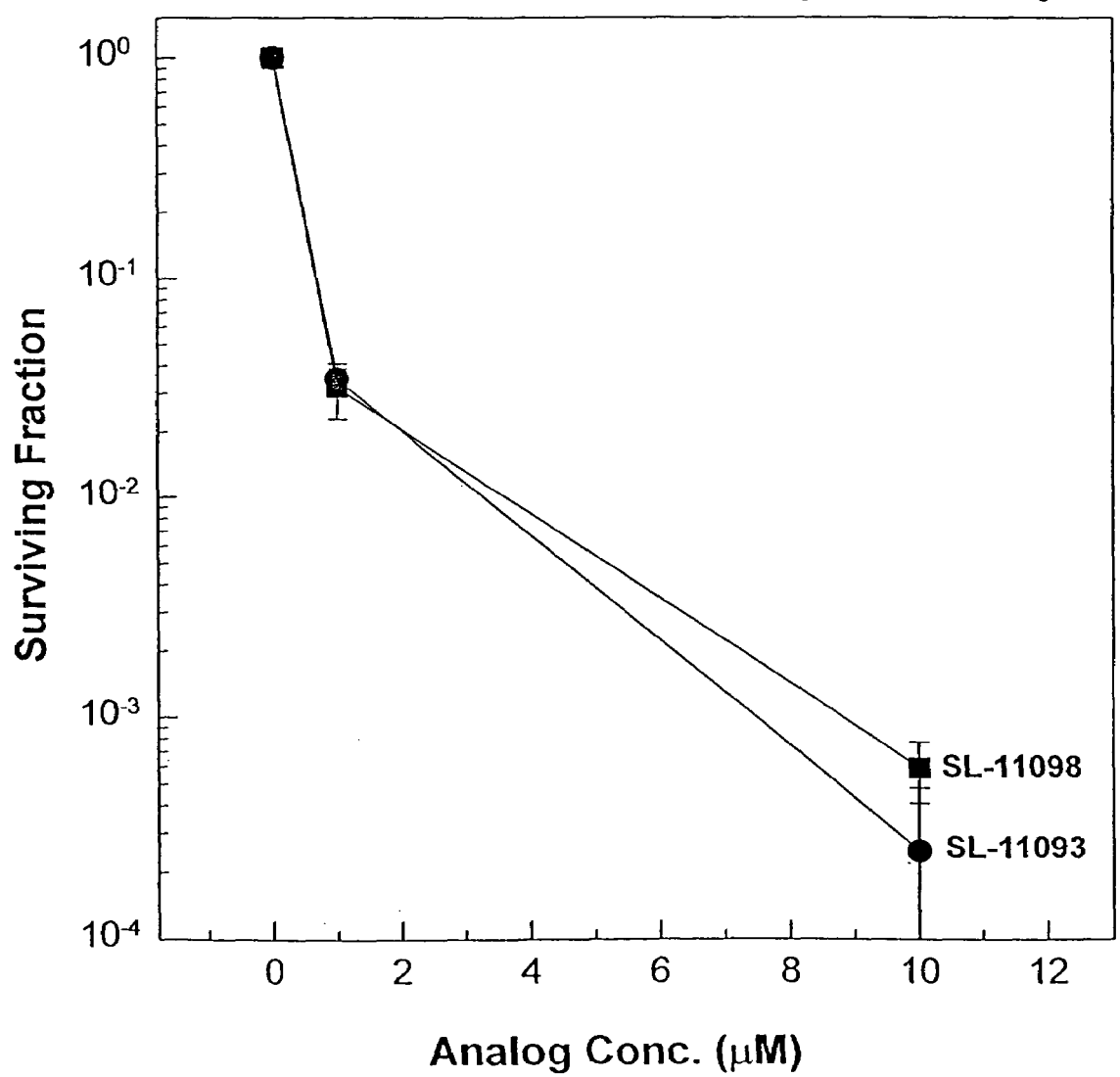
FIG. 2 is a graph depicting the effect of SL-11093 and SL-11098 on DuPro human prostate tumor cell survival by CFE assay.
Figure 3:
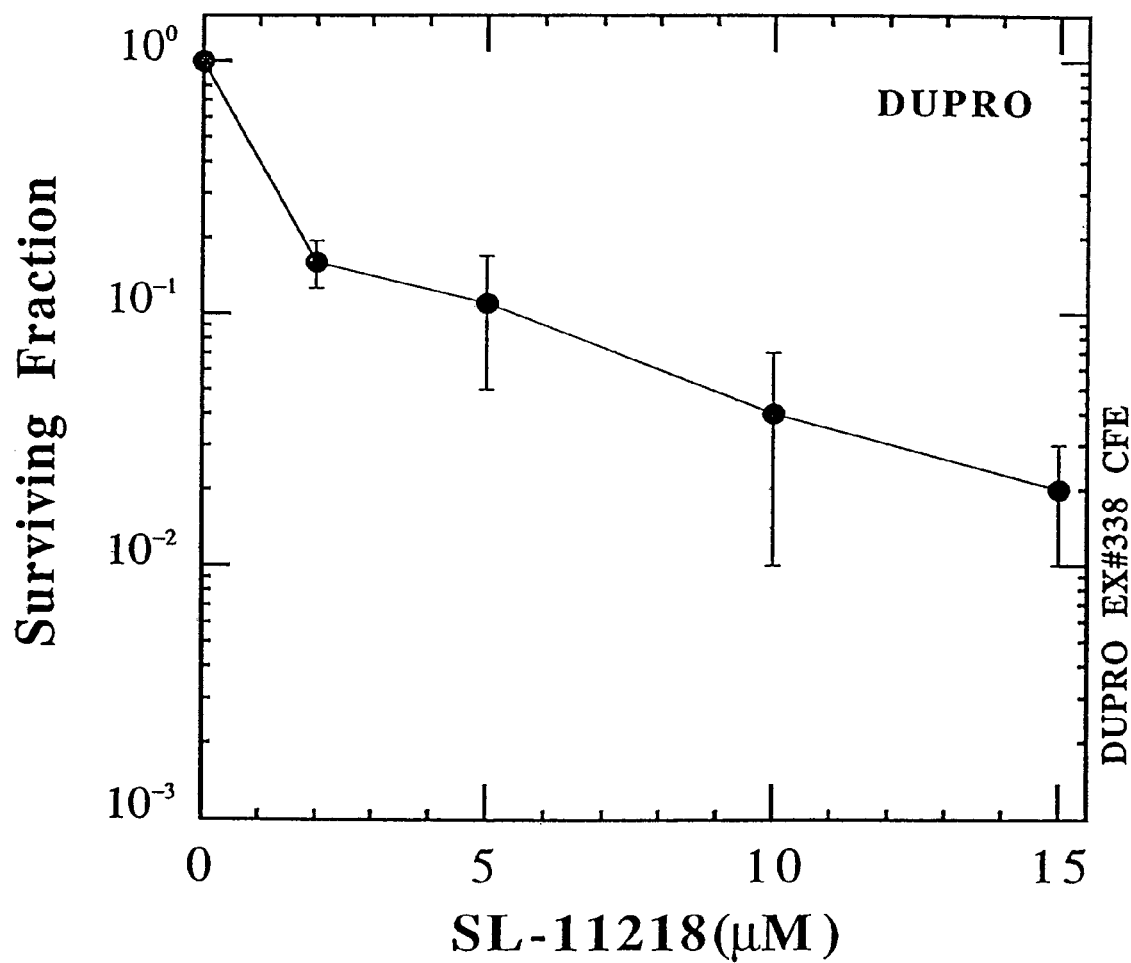
FIG. 3 is a graph depicting the effect of SL-11218 cytoxicity in DuPro cells after 5 days incubation.
Figure 4:
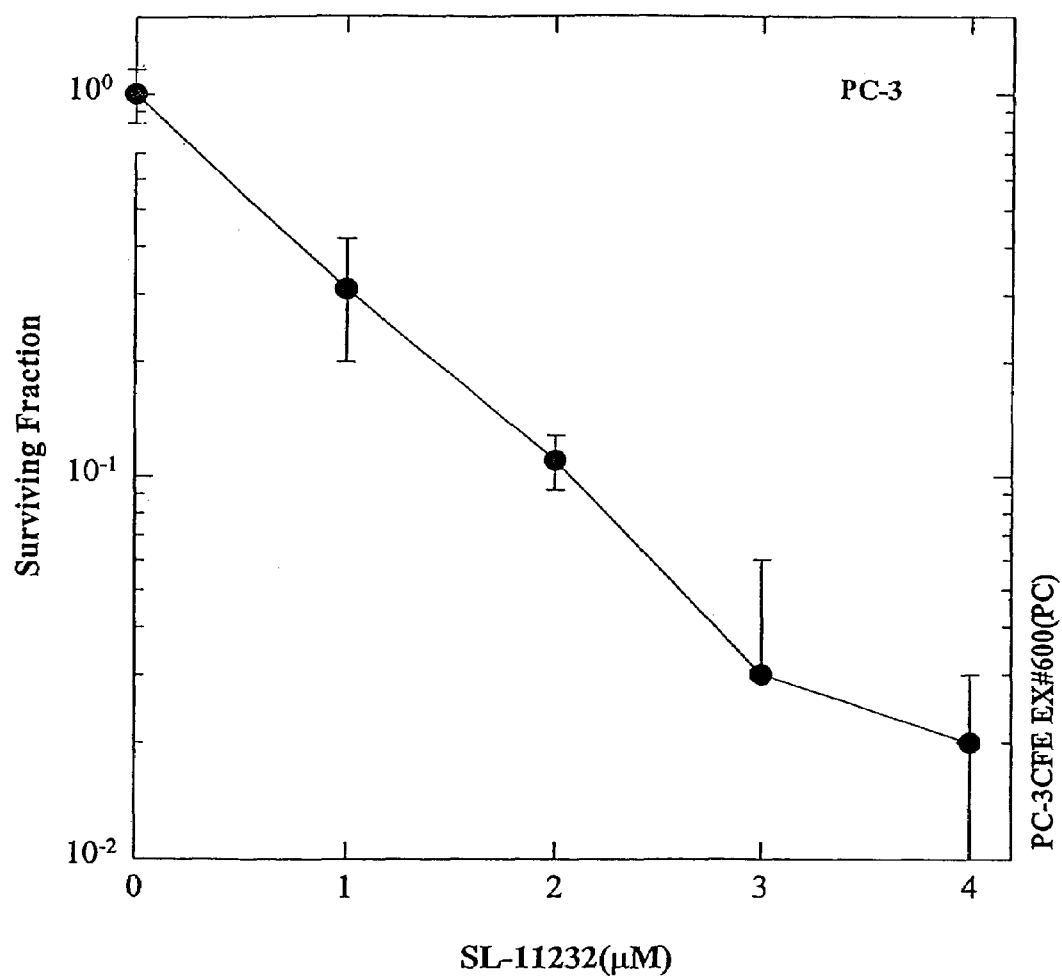
FIG. 4 is a graph depicting the effect of SL-11232 in PC-3 cells after 5 days of incubation.
Figure 5:
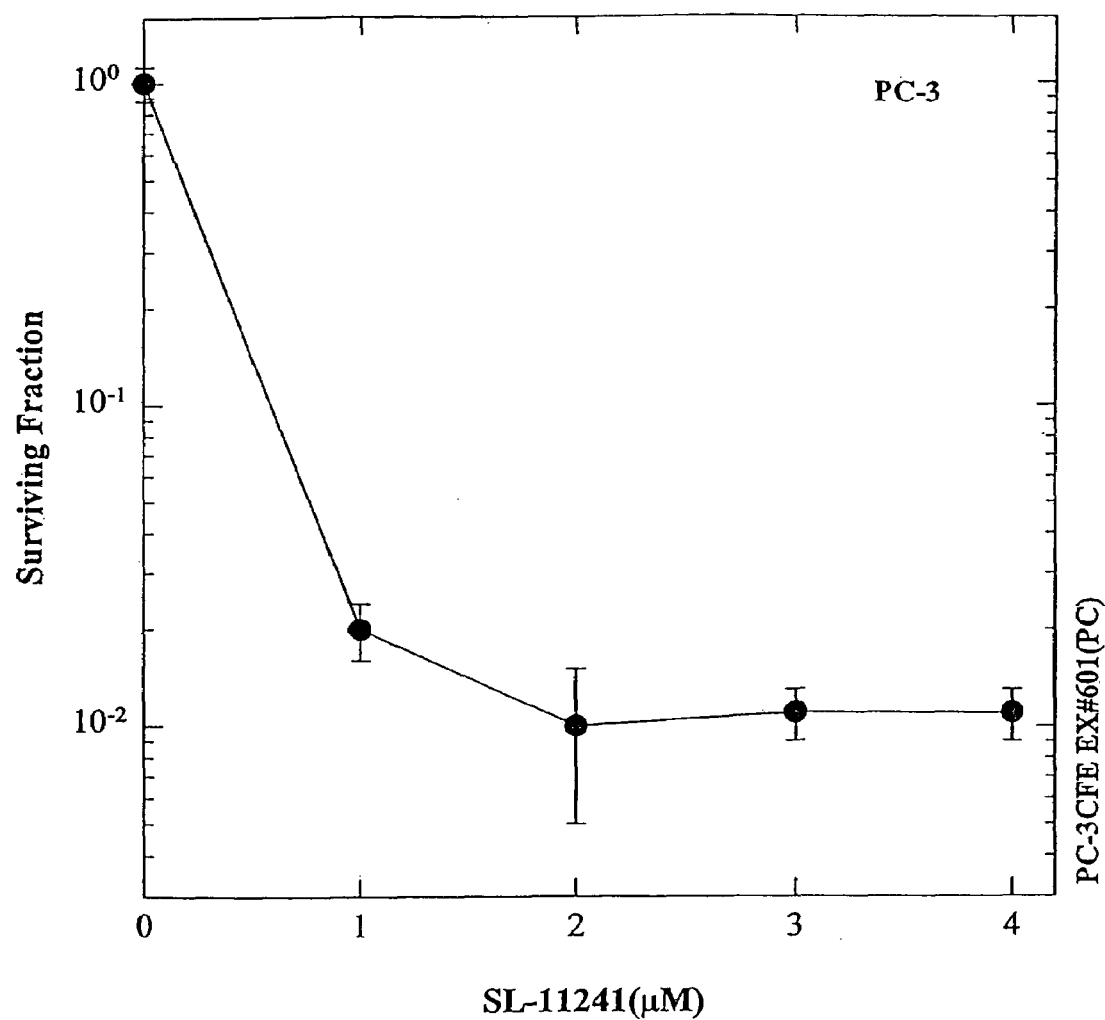
FIG. 5 is a graph depicting the effect of SL-11241 in PC-3 cells after 5 days of incubation.

The invention is directed to various novel polyamine analogs and methods of making them as described herein. The invention includes all salts of the compounds described herein. Particularly preferred are pharmaceutically acceptable salts. Pharmaceutically acceptable salts are those salts which retain the biological activity of the free bases and which are not biologically or otherwise undesirable. The desired salt may be prepared by methods known to those of skill in the art by treating the polyamine with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of the polyamines with amino acids, such as aspartate salts and glutamate salts, can also be prepared.

The invention also includes all stereoisomers of the compounds, including diastereomers and enantiomers, as well as mixtures of stereoisomers, including, but not limited to, racemic mixtures. Unless stereochemistry is explicitly indicated in a structure, the structure is intended to embrace all possible stereoisomers of the compound depicted.

The term "polyamine" in its most general sense refers to a compound containing more than one amino group. As used herein, "polyamine" is used to refer to any one of a group of aliphatic, straight-chain amines derived biosynthetically from amino acids; such polyamines are reviewed in Marton et al. (1995) Ann. Rev. Pharm. Toxicol. 35:55–91. By "polyamine analog" is meant a compound containing two or more amino groups, where the amino groups are linked by substituted or unsubstituted hydrocarbon moieties. The hydrocarbon moieties can be substituted or unsubstituted alkyl, alkenyl, alkynyl, cycloalkyl, cycloalkenyl, cycloalkynyl, or aryl groups, or any combination thereof. Polyamine analogs can be structurally similar to the naturally-occurring polyamines such as spermine and/or spermidine and their precursor, the diamine putrescine. Polyamine analogs can be branched or un-branched.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, and adamantyl. Cyclic groups can consist of one ring, including, but not limited to, groups such as cycloheptyl, or multiple fused rings, including, but not limited to, groups such as adamantyl or norbornyl.

"Substituted alkyl" refers to alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —CF$_3$, —CF$_2$—CF$_3$, and other perfluoro and perhalo groups.

"Hydroxyalkyl" specifically refers to alkyl groups having the number of carbon atoms specified substituted with one —OH group. Thus, "C$_3$ linear hydroxyalkyl" refers to —CH$_2$CH$_2$CHOH—, —CH$_2$CHOHCH$_2$—, and —CHOHCH$_2$CH$_2$—.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). Examples of alkenyl groups include, but are not limited to, —CH$_2$—CH=CH—CH$_3$; and —CH$_2$—CH$_2$-cyclohexenyl, where the ethyl group can be attached to the cyclohexenyl moiety at any available carbon valence. The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, alkynyl, or aryl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Aryl" or "Ar" refers to an aromatic carbocyclic group having a single ring (including, but not limited to, groups such as phenyl) or multiple condensed rings (including, but not limited to, groups such as naphthyl or anthryl), and includes both unsubstituted and substituted aryl groups. "Substituted aryls" refers to aryls substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$, —CH$_2$—CH$_2$—NH—CH$_2$—CH$_2$—, 1-ethyl-6-propylpiperidino, 2-ethylthiophenyl, and morpholino. Examples of heteroalkenyl groups include, but are not limited to, groups such as —CH=CH—NH—CH(CH$_3$)—CH$_2$—. "Heteroaryl" or "HetAr" refers to an aromatic carbocyclic group having a single ring (including, but not limited to, examples such as pyridyl, thiophene, or furyl) or multiple condensed rings (including, but not limited to, examples such as imidazolyl, indolizinyl or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twenty carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—SO$_2$-phenyl, —NH—(C=O)O-alkyl, —NH—(C=O)O-alkyl-aryl, and —NH—(C=O)-alkyl. If chemically possible, the heteroatom(s) as well as the carbon atoms of the group can be substituted. The heteroatom(s) can also be in oxidized form, if chemically possible.

The term "alkylaryl" refers to an alkyl group having the number of carbon atoms designated, appended to one, two, or three aryl groups.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The term "alkanoate" as used herein refers to an ionized carboxylic acid group, such as acetate (CH$_3$C(=O)—O$^{(-1)}$), propionate (CH$_3$CH$_2$C(=O)—O$^{(-1)}$), and the like. "Alkyl alkanoate" refers to a carboxylic acid esterified with an alkoxy group, such as ethyl acetate (CH$_3$C(=O)—O—CH$_2$CH$_3$). "ω-haloalkyl alkanoate" refers to an alkyl alkanoate bearing a halogen atom on the alkanoate carbon atom furthest from the carboxyl group; thus, ethyl ω-bromo propionate refers to ethyl 3-bromopropionate, methyl ω-chloro n-butanoate refers to methyl 4-chloro n-butanoate, etc.

The terms "halo" and "halogen" as used herein refer to Cl, Br, F or I substituents.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 2nd Ed. (John Wiley & Sons, Inc., New York). Amino protecting groups include, but are not limited to, mesitylenesulfonyl (Mes), benzyloxycarbonyl (CBz or Z), t-butyloxycarbonyl (Boc), t-butyldimethylsilyl (TB-DIMS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Hydroxyl protecting groups include, but are not limited to, Fmoc, TBDIMS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

In one embodiment, the invention encompasses improved methods for making cyclopropyl-containing polyamines. One such method utilizes addition of a carbene-bearing compound, or a carbene equivalent-bearing compound, to a double bond of an alkene compound, as one of the steps in the synthetic method.

In another embodiment, the polyamine compound synthesized by the methods of the invention is selected from among the group of compounds of the formula:

E-NH-B-A-B-NH-B-A-B-NH-B-A-B-NH(-B-A-B-NH)$_x$-E where A is independently selected from the group consisting of a single bond, $C_2$–$C_6$ alkyl, $C_2$–$C_6$ hydroxyalkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; B is independently selected from the group consisting of a single bond, $C_1$–$C_6$ alkyl, $C_1$–$C_6$ hydroxyalkyl, and $C_2$–$C_6$ alkenyl; E is independently selected from the group consisting of H, $C_1$–$C_6$ alkyl, $C_1$–$C_6$ hydroxyalkyl, $C_2$–$C_6$ alkenyl, and $C_2$–$C_6$ alkynyl; and x is an integer from 0 to 16; with the proviso that at least one A moiety is cyclopropyl, and that every -B-A-B- subunit contains at least two carbon atoms; and all salts and stereoisomers thereof.

Alkene compounds are well-defined in the art as compounds containing one or more double bonds; the term "olefinic compounds" is also used and is synonymous with "alkenes."

Carbene compounds are well-known in the art. The term "carbenoid" is used when a free carbene reactant is not present, or when presence of a free carbene cannot be demonstrated or is in doubt. Carbene-equivalent compounds are defined as including both carbenoids, and compounds with a single reactive carbon where that single carbon forms two bonds (either one double bond or two single bonds) to another compound. Thus, carbene-equivalent compounds include (but are not limited to) compounds such as ylides, which can react with double bonds in a manner analogous to the carbene reaction with double bonds, even though the actual mechanism by which ylides react with double bonds is believed to be nucleophilic addition.

The reaction of carbenes or carbene-equivalent compounds with alkenes is well-known in the art and proceeds as follows in reaction (IV):

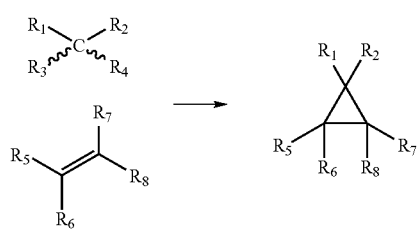

(IV)

where the single carbon atom to which $R_1$, $R_2$, $R_3$, and $R_4$ was attached has formed two bonds to the alkene compound (losing $R_3$ and $R_4$ in the process; it should be noted that $R_3$ and $R_4$ may be two separate substituents, or that $R_3$ or $R_4$ may be a formal negative charge instead of a substituent, or $R_3$ and $R_4$ may together be a double bond to one substituent) where the resulting stereochemistry of the groups $R_1$, $R_2$, $R_5$, $R_6$, $R_7$, and $R_8$ depends on the specific characteristics of the reagents. For the sulfur ylide reaction (V):

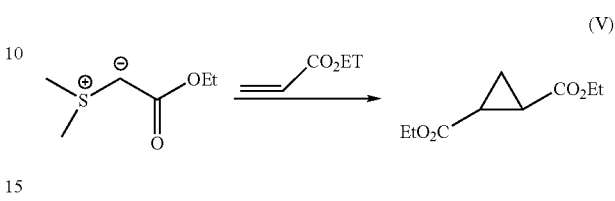

(V)

the E-isomer of the cyclopropyl diester is the only product (see Example 1).

The ylide reaction (VI):

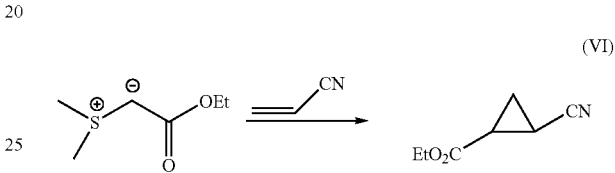

(VI)

yields ethyl 2-cyanocyclopropanecarboxylate, which can be used as starting material in Example 6 below. While the above two examples produce trans-isomers of cyclopropane, methods are known in the art by which cis-isomers of cyclopropane can be synthesized (see, e.g., Hamaker, C G et al., (2001) Organometallics 20(10):2102–2108; Doyle, M P et al., (1993) Helv. Chim. Acta 76(6):2227–2235; Nguyen, S T and Jin, W (1999), Book of Abstracts, 218th ACS National Meeting, New Orleans, Aug. 22–26, 1999, INOR-104, Publisher: American Chemical Society, Washington, D.C.).

After the reaction of the carbene or carbene-equivalent compound with the alkene, the various functional groups on the molecule ($R_1$, $R_2$, $R_5$, $R_6$, $R_7$, and $R_8$) can be derivatized further if they are suitably reactive. For the sulfur ylide reaction (V) depicted above, $R_1$ is —COOEt, $R_2$ is —H, $R_5$ is —COOEt, and $R_6$, $R_7$, and $R_8$ are —H, forming trans-1,2-diethoxycarbonyl cyclopropane (diethyl trans-1,2-cyclopropane dicarboxylate). The ester groups can undergo further chemical reactions under conditions that do not destroy the cyclopropyl group. In Example 1, below, the ester groups are converted into carboxylic acid groups; the carboxylic acid groups are then converted into acid chloride groups. The carboxylic acid groups can, of course, be converted into other reactive acyl groups of the form —C(=O)—X, where X is a good leaving group. X can be a halide, p-nitrophenol, N-hydroxysuccinimide, HOBt (1-hydroxybenzotriazole) or HOAt (1-hydroxy-7-azabenzotriazole) where the hydroxyl oxygen of HOBt or HOAt is attached to the acyl group, or any one of a number of other good leaving groups. The active esters can then be reacted with amino groups or other nucleophiles, and further chemistry can be performed on the resulting compounds.

Alternatively, the diethyl trans-1,2-cyclopropane dicarboxylate can be reduced to trans-1,2-bis(hydroxymethyl) cyclopropane, as described in Example 2 below. The resulting diol can be converted to a dibromide, or alternatively, the alcohols can be converted to other leaving groups, such as other halides, tosylates, mesitylates, or mesylates. The electrophilic bromide-bearing (or other leaving-group bearing) carbons can then be reacted with amines or other nucleophiles, and further chemistry can be performed on the resulting compounds.

Amines, amides, and sulfonamides which can be reacted with the electrophilic cyclopropane derivatives include, but are not limited to, compounds of the form R—NH$_2$ and R—NH-PG, where R is a hydrocarbon moiety and PG denotes a protecting group. When PG is a mesitylene group, R—NH-PG is of the form R—NH—S(=O)$_2$-2,4,6-trimethylbenzene, that is, the nitrogen of the compound is a sulfonamide. Various non-limiting examples of amines, amides, and sulfonamides which can be reacted with the electrophilic cyclopropane derivatives are given in the Examples below, and they can be combined in any fashion to form cyclopropane-containing polyamines. Multiple cyclopropane groups can be incorporated into the polyamines in a manner analogous to that depicted in Examples 2, 3, and 6 below.

Hydroxyalkyl units can be added to the molecule by various methods. Example 7 below illustrates one method, where 2-Hydroxy-γ-butyrolactone 120 was used as a starting material. (This compound is commercially available as both R and S isomers.) Following the protection of hydroxy group with t-butyldimethylsilyl chloride (TBDMSCl), the resulting lactone 121 was treated with a THF solution of EtNH$_2$. The resulting hydroxy amide 122 was subjected to a Mitsunobu reaction with phthalimide (PhTh), diethylazodicarboxylate (DEAD), and triphenylphosphine, followed by deprotection with hydrazine to obtain amine 123.

Therapeutic use of Polyamine Analogs

Polyamine analogs of the present invention are useful for treatment of a variety of diseases caused by uncontrolled proliferation of cells, including cancer, particularly prostate cancer and other cancer cell lines. The compounds are used to treat mammals, preferably humans. "Treating" a disease using an polyamine analog of the invention is defined as administering one or more polyamine analogs of the invention, with or without additional therapeutic agents, in order to prevent, reduce, or eliminate either the disease or the symptoms of the disease, or to retard the progression of the disease or of symptoms of the disease. "Therapeutic use" of the polyamine analogs of the invention is defined as using one or more polyamine analogs of the invention to treat a disease, as defined above.

In order to evaluate the efficacy of a particular polyamine analog for a particular medicinal application, the compounds can be first tested against appropriately chosen test cells in vitro. In a non-limiting example, polyamine analogs can be tested against tumor cells, for example, prostate tumor cells. Exemplary experiments can utilize cell lines capable of growing in culture as well as in vivo in athymic nude mice, such as LNCaP. Horoszewicz et al. (1983) *Cancer Res.* 43:1809–1818. Culturing and treatment of carcinoma cell lines, cell cycle and cell death determinations based on flow cytometry; enzyme assays including ODC, SAMDC and SSAT activities; and high pressure liquid chromatography detection and quantitation of natural polyamines and polyamine analogs are described in the art, for example, Mi et al. (1998) *Prostate* 34:51–60; Kramer et al. (1997) *Cancer Res.* 57:5521–27; and Kramer et al. (1995) *J. Biol. Chem.* 270:2124–2132. Evaluations can also be made of the effects of the polyamine analog on cell growth and metabolism.

Analysis begins with IC$_{50}$ determinations based on dose-response curves ranging from 0.1 to 1000 µM performed at 72 hr. From these studies, conditions can be defined which produce about 50% growth inhibition and used to: (a) follow time-dependence of growth inhibition for up to 6 days, with particular attention to decreases in cell number, which may indicate drug-induced cell death; (b) characterize polyamine analog effects on cell cycle progression and cell death using flow cytometry (analysis to be performed on attached and detached cells); (c) examine polyamine analog effects on cellular metabolic parameters. Polyamine analog effects can be normalized to intracellular concentrations (by HPLC analysis), which also provide an indication of their relative ability to penetrate cells. Marked differences in polyamine analog uptake can be further characterized by studying the compound's ability to utilize and regulate the polyamine transporter, as assessed by competition studies using radiolabeled spermidine, as previously described in Mi et al. (1998). Polyamine analogs could also enter the cells by a diffusion mechanism.

In vivo Testing of Polyamine Analogs

Polyamine analogs found to have potent anti-proliferative activity in vitro towards cultured carcinoma cells can be evaluated in in vivo model systems. The first goal is to determine the relative toxicity of the compounds in non-tumor-bearing animals, such as DBA/2 mice. Groups of three animals each can be injected intraperitoneally with increasing concentrations of an polyamine analog, beginning at, for example, 10 mg/kg. Toxicity as indicated by morbidity is closely monitored over the first 24 hr. A well-characterized polyamine analog compound, such as BE-333, can be used as an internal standard in these studies, since a data base has already been established regarding acute toxicity via a single dose treatment relative to chronic toxicity via a daily×5 d schedule. Thus, in the case of polyamine analogs, single dose toxicity relative to BE-333 is used to project the range of doses to be used on a daily×5 d schedule.

After the highest tolerated dosage on a daily×5 d schedule is deduced, antitumor activity is determined. Typically, tumors can be subcutaneously implanted into nude athymic mice by trocar and allowed to reach 100–200 mm$^3$ before initiating treatment by intraperitoneal injection daily×5 d. Most polyamine analogs can be given in a range between 10 and 200 mg/kg. Polyamine analogs can be evaluated at three treatment dosages with 10–15 animals per group (a minimum of three from each can be used for pharmacodynamic studies, described below). Mice can be monitored and weighed twice weekly to determine tumor size and toxicity. Tumor size is determined by multi-directional measurement from which volume in mm$^3$ is calculated. Tumors can be followed until median tumor volume of each group reaches 1500 mm$^3$ (i.e., 20% of body weight), at which time the animals can be sacrificed. Although the initial anti-tumor studies focuses on a daily×5 d schedule, constant infusion can be performed via Alzet pump delivery for 5 days since this schedule dramatically improves the anti-tumor activity of BE-333 against A549 human large cell hung carcinoma. Sharma et al. (1997) *Clin. Cancer Res.* 3:1239-1244. In addition to assessing anti-tumor activity, free polyamine analog levels in tumor and normal tissues can be determined in test animals.

Methods of Administration of Polyamine Analogs

The polyamine analogs of the present invention can be administered to a mammalian, preferably human, subject via any route known in the art, including, but not limited to, those disclosed herein. Methods of administration include but are not limited to, intravenous, oral, intraarterial, intratumoral, intramuscular, topical, inhalation, subcutaneous, intraperitoneal, gastrointestinal, and directly to a specific or affected organ. The polyamine analogs described herein are administratable in the form of tablets, pills, powder mixtures, capsules, granules, injectables, creams, solutions, suppositories, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the novel polyamine analog(s) to retain its pharmacological activity in the body. Formulations for parenteral and nonparenteral drug delivery are known in the art and are set forth in *Remington's Pharmaceutical Sciences,* 18th Edition, Mack Publishing (1990). Solid forms, such as tablets, capsules and powders, can be fabricated using conventional tableting and capsule-filling machinery, which is well known in the art. Solid dosage forms, including tablets and capsules for oral administration in unit dose presentation form, can contain any number of additional non-active ingredients known to the art, including such conventional additives as excipients; desiccants; colorants; binding agents, for example syrup, acacia, gelatin, sorbitol, tragacanth, or polyvinylpyrollidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulfate. The tablets can be coated according to methods well known in standard pharmaceutical practice. Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, polyamine analogs can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (e.g., peanut oil, soy bean oil), petroleum-derived oils (e.g., mineral oil), and synthetic oils. In general, for injectable unit doses, water, saline, aqueous dextrose and related sugar solutions, and ethanol and glycol solutions such as propylene glycol or polyethylene glycol are preferred liquid carriers. The pharmaceutical unit dosage chosen is preferably fabricated and administered to provide a final concentration of drug at the point of contact with the cancer cell of from 1 µM to 10 mM. More preferred is a concentration of from 1 to 100 µM. The optimal effective concentration of polyamine analogs can be determined empirically and will depend on the type and severity of the disease, route of administration, disease progression and health and mass or body area of the patient. Such determinations are within the skill of one in the art. Polyamine analogs can be administered as the sole active ingredient, or can be administered in combination with another active ingredient, including, but not limited to, cytotoxic agents, antibiotics, antimetabolites, nitrosourea, vinca alkaloids, polypeptides, antibodies, cytokines, etc.

EXAMPLES

The following examples are provided to illustrate the methods of the invention, and are not to be construed as limiting the invention in any manner.

The synthesis of SL-11093, a $^1$N,$^{14}$N-(bisethyl)homospermine analog where the conformational restriction is due to a trans-cyclopropyl ring, is described in Example 1. Condensation of dimethyl sulfide and ethyl bromoacetate gave the bromide 1. In alkali medium it formed the ylid 2. Condensation of 2 with ethyl acrylate gave only the trans-cyclopropane diester 3. Saponification of 3 gave the diacid 4 which was transformed into the dichloride 5. Condensation of 5 with the amide 6 gave tetramide 7. Reduction of the peptide bonds with diborane, followed by deprotection of the nitrogen residues gave 8, SL-11093 tetrahydrochloride.

SL-1231 hexachloride (synthesis described in Example 2) was obtained by condensation of 11 and 13 to give the hexamide 20. Deprotection of the latter gave 21, i.e., SL-11231 hexachloride.

The synthesis of SL-11242 and the ter-cyclopropyloligoamine SL-11232 is described in Example 3. Starting with the trans-1,2-dibromomethyl-cyclopropane 9 and by condensation with diamide 10, it was possible to obtain 11. Reaction of the bromomethyl derivative 11 with dimesityleneputrescine 13 gave the tetramide 14. In tandem, by condensation of 9 with mesitylene amide it was possible to obtain 12. Dialkylation of 12 with 1,4-dibromobutane gave 15. Condensation of 15 with 14 gave the decamide 16. Deprotection of the sulfonamide groups with hydrogen bromide gave decamine 17 (SL-11232), isolated as its decahydrochloride. Deprotection of tetramide 14 gave 18, SL-11242 tetrahydrochloride (Scheme 3).

The synthesis of the cyclopropyl decamine SL-11241 was achieved by condensation of diester 22 with pentamide 23 (see Example 4). Decamide 24 thus obtained, it was deprotected to give 25; i.e., SL-11241 decahydrochloride.

The synthesis of SL-11247 and SL-11245 is described in Example 5. Bis-N,N'-tert-butyl tetramine SL-11247 was prepared starting with t-butylmesityleneamide 26 which was alkylated with 4-bromobutyronitrile to give 27. The latter was reduced to 28 and the free amino residue was protected to give 29. Condensation with 22 gave the tetramide 30. Cleavage of the protecting groups in 30 in alkali medium gave 32 (SL-11247) while cleavage in acid gave 31, SL-11245 tetrahydrochloride.

SL-11215 tetrahydrochloride was obtained as described in Example 6. Starting with the known trans-cyclopropyl derivative 33, it was reduced with lithium borohydride to the alcohol, and the latter esterified to give 34. Alkylation of ethyl mesityleneamide with 34 gave 35, which was reduced to the aminomethyl derivative and protected to give 36. Alkylation of 36 with 22 gave the tetramide 37, which was deprotected to 38; i.e., SL-11215 tetrahydrochloride.

By reaction of 36 with the diester 39, tetramide 40 was obtained. When deprotected, it gave 41, SL-11218 tetrahydrochloride.

Example 1

Synthesis of SL-11093

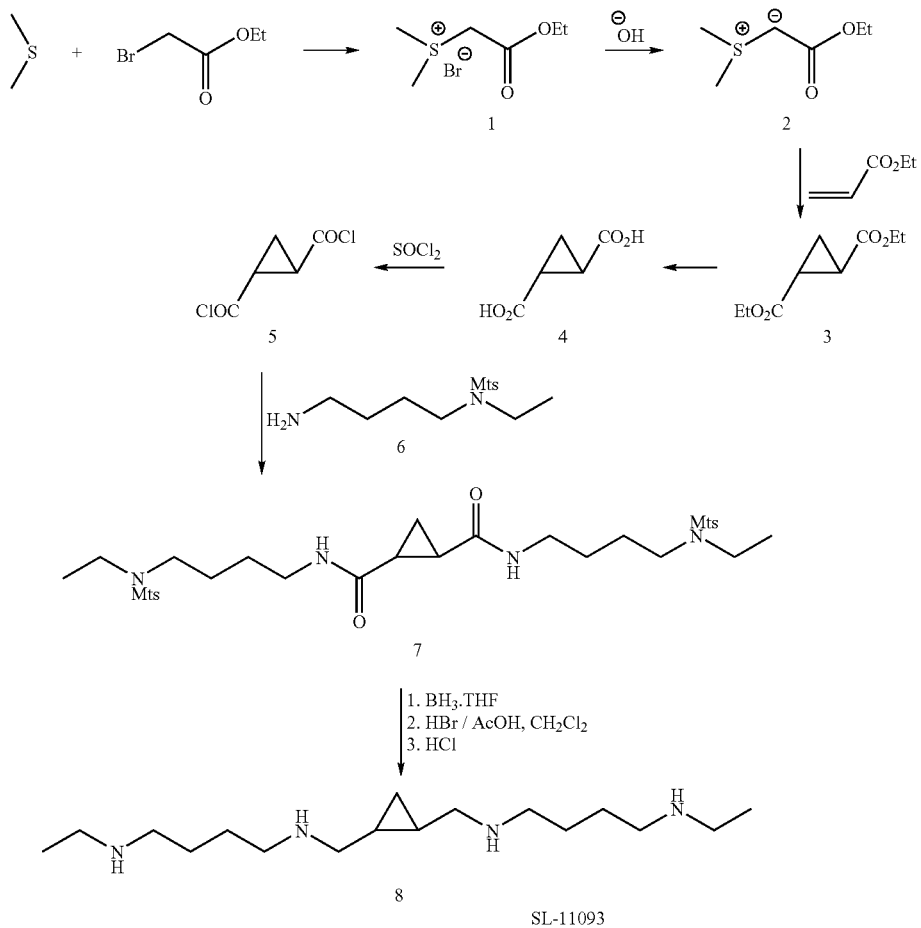

SL-11093

(Ethoxycarbonylmethyl)dimethylsulfonium bromide 1

A stirred solution of ethyl bromoacetate (98%, 287 g, 1.68 mol) and methyl sulfide (99%, 156 mL, 1.25 eq.) in acetone (500 mL) was kept at 15° C. A white precipitate started to appear immediately and became thicker upon stirring. After stirring for 18 h at 22° C., the solid was filtered, washed with acetone (3×100 mL), and dried under vacuum to afford 1 (477 g, 83.4%) as white crystals. $^1$H NMR (250 MHz, CDCl$_3$) δ 5.20 (s, 2H); 4.29 (q, J=7.2, 2H); 3.46 (s, 6H); 1.32 (t, J=7.2, 3H). $^{13}$C NMR (62.5 MHz, CDCl$_3$) δ 164.36; 63.38; 44.38; 25.22; 13.92.

(Ethoxycarbonylmethyl)dimethylsulfonium ylid 2

A mixture of 50% aqueous NaOH (183 g) and saturated K$_2$CO$_3$ (1970 g) was added to a stirred solution of 1 (476 g, 2.08 mol) in CHCl$_3$ over a period of 15 min at 10° C. After stirring for an additional 1 h, the top organic layer was decanted, dried over K$_2$CO$_3$ for 30 min, filtered, and concentrated to give 2 (282 g, 91.7%) as a pale yellow oil. $^1$H NMR (250 MHz, CDCl$_3$) δ 4.04 (q, J=7.1, 2H); 2.90 (s, 1H); 2.76 (s, 6H); 1.24 (t, J=7.1, 3H). $^{13}$C NMR (62.5 MHz, CDCl$_3$) δ 170.25; 77.20; 57.83; 31.58; 30.62; 14.89.

trans-1,2-diethoxycarbonyl-cyclopropane 3

Ethyl acrylate (99%, 270 g, 1.4 eq.) was added to a solution of 2 (282 g, 1.91 mol) in CHCl$_3$ (1500 mL) at 5° C. Cooling was removed and the reaction was stirred at 22° C. for 12 h. Evaporation of the solvent and excess acrylate left an orange oil, which was vacuum distilled (bp 70–75° C./1 mm) to produce 3 (286 g, 80.6%) as a clear thick oil. $^1$H NMR (250 MHz, CDCl$_3$) δ 4.15 (q, J=7.1, 4H); 2.16 (dd, J=7.5, 5.7, 2H); 1.41 (dd, J=7.5, 5.7, 2H); 0.88 (t, J=7.1, 6H). $^{13}$C NMR (62.5 MHz, CDCl$_3$) δ 171.69; 60.96; 22.26; 15.18; 14.08.

trans-1,2-Cyclopropanedicarboxylic acid 4:

Diethyl carboxylate 3 (16.9 g, 19.3 mmol) was dissolved in 170 ml of 2N NaOH and heated under reflux for 1 h. The solution was stirred for additional 18 h at 22° C. The solution was cooled, adjusted to pH 3 with 2N HCl, saturated with NaCl, and finally extracted with ethyl acetate (2×100 ml). The pooled extracts were dried (Na$_2$SO$_4$), evaporated to dryness, and the white residue was used for the next step without further purification (8.5 g, 79%); mp 175–176° C. $^1$H-NMR (D$_2$O): δ 1.42 (m, 2H), 2.18 (m, 4H).

trans-1,2-Dichlorocarbonylcyclopropane 5:

Dicarboxylic acid 4 (3.4 g, 26.12 mmol) was dissolved in 10 ml of thionyl chloride under nitrogen, and the solution was stirred and heated at 60° C. for 4 h. Excess thionyl chloride was distilled off under reduced pressure, and the residue was distilled (40° C./0.1 mm) to give 2.9 g (71%) of the dichloride; $^1$H-NMR (CDCl3): δ 1.90 (m, 2H), 2.91 (m, 2H).

N,N'-Bis-(4-N-(mesitylene)N-ethylbutylamine)-trans-1,2-cyclopropanediamide 7.

Amide 6 (6.3 g, 21 mmol; prepared as described in Reddy et al (2001) J. Med. Chem. 44, 404–417) was dissolved in THF (100 ml), 3 ml of triethylamine were added, the mixture was cooled at 5° C., and dichloride 5 (1.77 g, 11 mmol) dissolved in 50 ml of dry THF was slowly added. The mixture was stirred for 30 min, 3 ml of triethylamine added, and stirring was continued for 18 h at 22° C. Ethyl acetate (100 ml) was then added, the solution was washed with 10% HCl (3×50 ml), then with brine (50 ml), the organic layer was separated, dried (MgSO$_4$), evaporated to dryness, and the residue crystallized from hexane/ethyl acetate (1/1); 4.0 g of 7 were obtained (73%); mp 135–136° C. $^1$H-NMR (CDCl$_3$) δ 1.01 (t, J=7.15 Hz, 6H), 1.29 (m, 2H), 1.50 (m, 8H), 1.88 (m, 2H), 2.30 (s, 6H), 2.58 (s, 12H), 3.20 (m, 12H), 6.08 (br, 2H), 6.94 (s, 4H); $^{13}$C-NMR (CDCl$_3$) δ 12.72, 12.90, 20.92, 22.75, 23.43, 24.99, 26.82, 39.20, 40.13, 44.76, 131.92, 140.10, 143.00, 171.80; MS-ESI (m/z): 691.4 (M$^+$+1).

SL-11093 tetrahydrochloride 8

Diamide 7 (2.0 g, 2.9 mmol) was dissolved in dry THF and 70 ml of 1M diborane in THF was added, the flask was tightly stoppered, and the solution was stirred for 24 h at 22° C. Hydrogen bromide (30%) in glacial acetic acid (10 ml) was then added, and the mixture stirred at 22° C. during 18 h. The THF was then removed in vacuo, and 15 ml of methylene chloride was added to the residual solution, followed by 6.4 g of phenol and 40 ml of hydrogen bromide in glacial acetic acid. The mixture was stirred during 18 h at 22° C., water (40 ml) was added to dissolve suspended particles, and the solution was washed with CH$_2$Cl$_2$ (4×50 ml). The aqueous layer was evaporated to dryness in vacuo, the residue dissolved first in 5 ml 1N NaOH, then 6 ml 19N NaOH added (oily base separates), and the mixture was extracted repeatedly with CHCl$_3$ (6×30 ml). The extracts were pooled, dried (MgSO$_4$), evaporated to dryness, the residue was dissolved in 15 ml of dry methanol and 10 ml of dry ether, the solution cooled at 5° C. and the hydrochloride of SL-11093 was precipitated by bubbling hydrogen chloride; 0.7 g (80% yield); identical by $^1$H-NMR; $^{13}$C-NMR; and MS to a reference sample prepared as described in Valasinas et al. (2001) J. Med. Chem. 44, 390–403.

Example 2

Synthesis of SL-11231

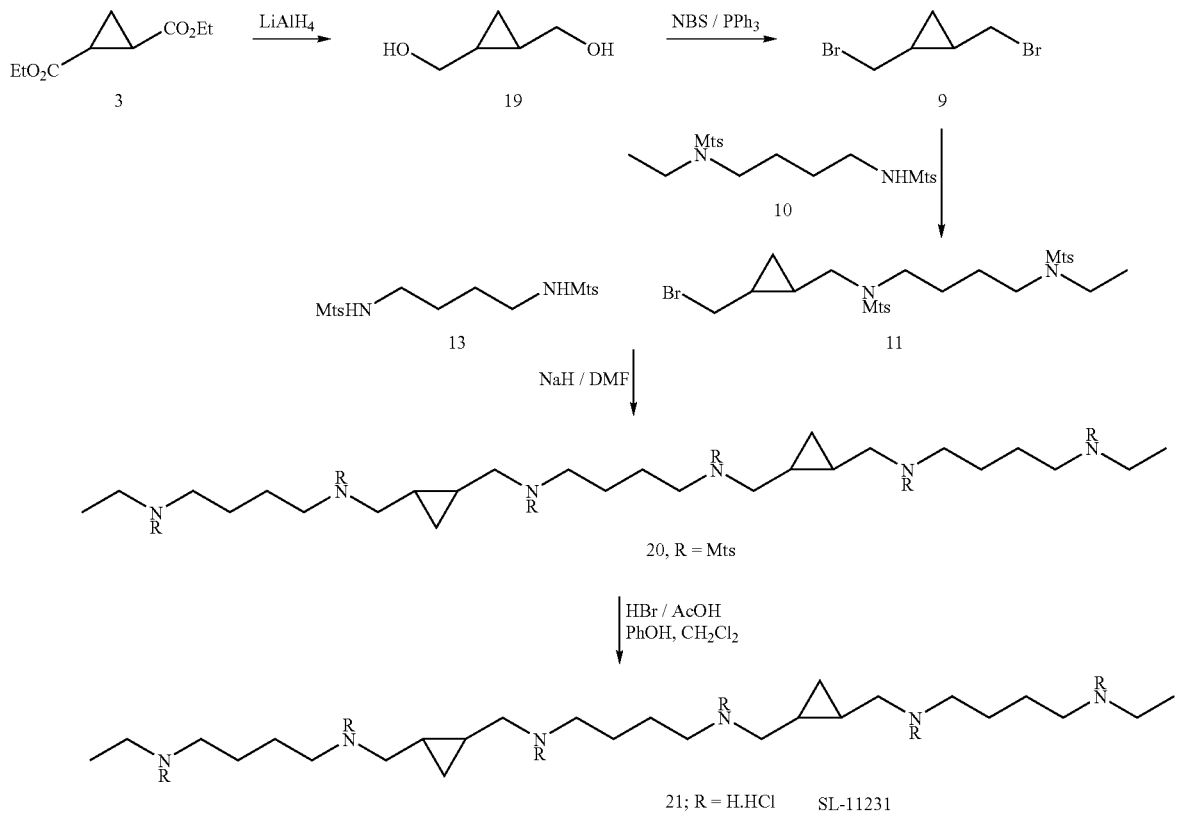

trans-1,2-Bis(bromomethyl)cyclopropane 9 trans-1,2-Bis(hydroxymethyl)cyclopropane 19 (2.6 g, 25 mmol, prepared as described in Reddy et al (1998) J. Med. Chem. 41, 4723) was dissolved in 60 ml of dry CH$_2$Cl$_2$ under argon, P(Ph)$_3$ (13 g, 50 mmol) was added, and the solution was cooled to 5° C. N-bromosuccinimide (9 g, 50 mmol) was added slowly with stirring, and the mixture was kept at 22° C. for 18 h, when the solution was evaporated to dryness. The residue was extracted with petroleum ether (bp 35–60° C.) (4×25 ml), the pooled extracts were cooled at 5° C., and the precipitated triphenylphosphine oxide was filtered off. The solution was evaporated to dryness and the residue 9 (4.7 g) was directly used in the next step without further purification; $^1$H-NMR (CDCl$_3$) δ: 0.85 (t, J=6.76 Hz, 2H), 1.33 (t, J=6.30 Hz, 2H), 3.35 (m, 4H); $^{13}$C-NMR (CDCl$_3$) δ: 17.27, 24.41, 36.75.

Bis(mesitylenesulfonyl)-12-bromo-10,11-[(E)-1,2-cyclopropyl]-3,8-diazadodecane 11

Amide 10 (8.5 g, 18 mmol; prepared as described in Valasinas et al (2001) J. Med. Chem. 44, 390) was dissolved in dry DMF (150 ml) and NaH (60% in oil, 0.85 g) was added. The mixture was stirred for 30 min at 22° C., when 9 (4.0 g, 18 mmol) dissolved in 40 ml dry DMF was added and the mixture was further stirred during 18 h. Water (10 ml) was added, the solution evaporated to dryness in vacuo, the residue was partitioned between CHCl$_3$ and a saturated NH$_4$Cl solution, the organic layer was separated, evaporated to dryness and the residual oil was purified by column chromatography on silica gel using hexane/ethyl acetate (1/1) as eluant; 2.7 g (26% yield) of 11 were recovered; $^1$H-NMR (CDCl$_3$) δ: 0.55 (m, 2H), 0.92 (m, 2H), 1.00 (t, J=7.05 Hz, 3H), 1.40 (m, 4H), 2.30 (s, 6H), 2.58 (s, 12H), 2.90–3.20 (m, 10H), 6.94 (s, 4H); $^{13}$C-NMR (CDCl$_3$) δ: 12.75, 13.74, 19.77, 20.92, 21.07, 22.75, 24.74, 24.80, 37.59, 40.09, 44.62, 45.27, 48.61, 131.91, 140.13, 142.21, 142.43.

3,8,13,18,23,28-Hexakis(mesitylenesulfonyl)-10,11-[(E)-1,2-cyclopropyl]-20,21-[(E)-1,2-cyclopropyl]-3, 8,13,18, 23,28-hexaazatriacontane 20

Amide 13 (0.85 g, 1.8 mmol) was dissolved in 50 ml of dry DMF, NaH (60% in oil, 0.15 g) was added, the mixture stirred for 30 min at 22° C., and the. bromomethyl derivative 11 (2.3 g, 3.7 mmol) dissolved in 25 ml of dry DMF was added. The mixture was stirred for 18 h at 22° C., and the work-up described for 11 was followed. Column chromatography using chloroform/ethyl acetate (9/1) as eluant gave 2.0 g (34% yield) of 20; $^1$H-NMR (CDCl$_3$) d : 0.31 (m, 4H), 0.72 (m, 4H), 0.97 (t, J=7.12 Hz, 6H), 1.26 (m, 12H), 2.29 (s, 18H), 2.54–2.55 (s, 36H), 2.80 (m, 4H), 3.15 (m, 20H), 6.92 (s, 12H); MS-MALDI (m/z); 1567.39 (M$^+$+Na).

SL-11231 Hexahydrochloride 21

Hexamide 20 (2.0 g ) was deprotected with hydrogen bromide in glacial acetic acid following the procedure described for the pentamides (Reddy et al, (2001), loc. cit.). SL-11231 hexachloride was crystallized from aqueous ethanol; 0.5 g (60% yield) were obtained; $^1$H-NMR (D$_2$O) δ: 0.86 (t, J=6.8 Hz, 4H), 1.23 (m, 4H), 1.29 (t, J=7.3 Hz, 6H), 1.78 (m, 12H), 2.89 (m, 4H), 3.15 (m, 20H); $^{13}$C-NMR (D$_2$O) δ: 12.48, 12.95, 16.14, 25.28, 45.36, 48.71, 49.05, 49.35, 53.12; MS-ESI (m/z): 453.6 (M$^+$+1).

Example 3

Synthesis of SL-11232 and SL-11242

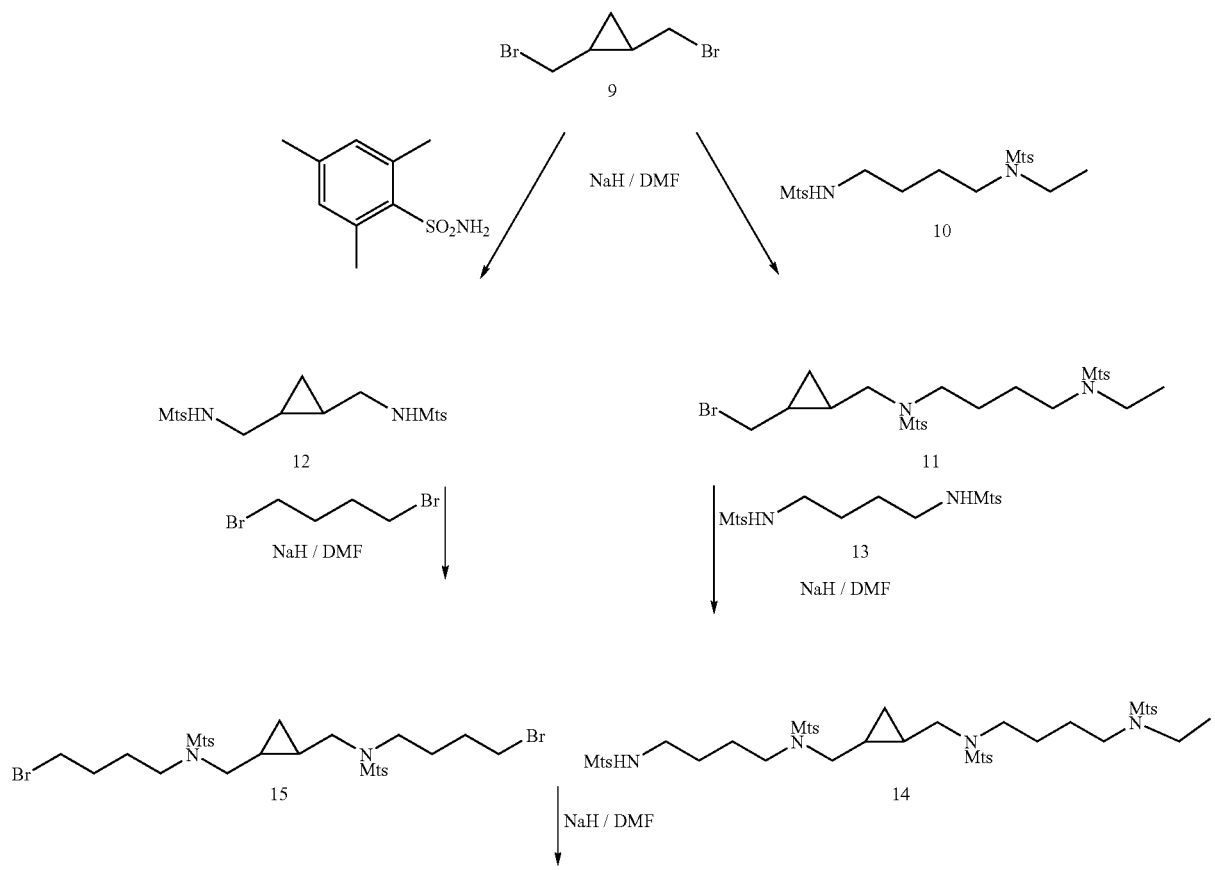

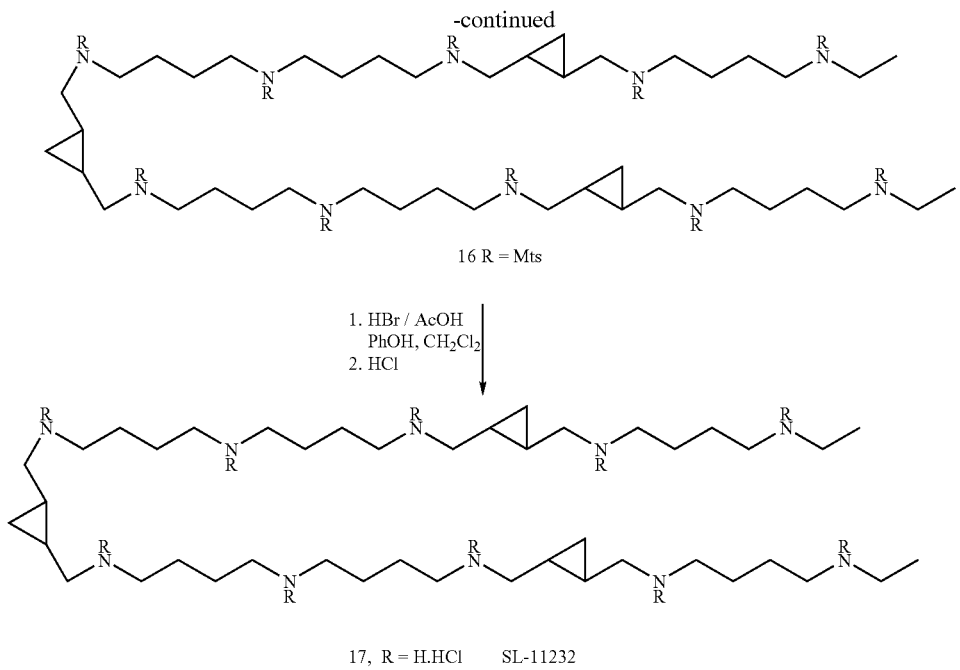

16 R = Mts

1. HBr / AcOH
   PhOH, CH₂Cl₂
2. HCl

17, R = H.HCl     SL-11232

3,8,13,18-Tetrakis(mesitylenesulfonyl)-10,11-[(E)-cyclopropyl]-3,8,13,18-tetraazaoctadecane 14

1,4-Bis(mesitylenesulfonyl)putrescine 13 (5.6 g, 12.4 mmol) and the bromomethyl derivative 11 from Example 2 (3.9 g, 6.2 mmol) were dissolved in 150 ml of dry DMF, and NaH (60%, 0.92 g) was added in one portion. The mixture was stirred for 18 h at 22° C., it was then quenched with 10 ml of 10% hydrochloric acid, the solution was evaporated to dryness, the residue was dissolved in CHCl₃ (100 ml), the latter washed first with water (2×50 ml), then with brine (50 ml); the organic solvent was evaporated to dryness and the residue purified by column chromatography on silica gel using CHCl₃/ethyl acetate (9/1) as eluant; 2.3 g (37% yield) of 14 were recovered; mp 63° C.; ¹H-NMR (CDCl₃) δ: 0.35 (m, 2H), 0.80 (m, 2H), 0.95 (t, J=5.8 Hz, 3H), 1.30–1.49 (m, 8H), 2.30 (s, 12H), 2.56 (s, 18H), 2.59 (s, 6H), 2.70–3.30 (m, 14H), 4.66 (t, J=6.4 Hz, 1H), 6.93 (s, 8H); MS-MALDI (m/z); 1021 (M⁺+Na).

5,10-Bis(mesitylenesulfonyl)-1,14-dibromo-7,8-[(E)-1,2-cyclopropyl]-5,10-diazatetradecane 15

Bis(mesitylenesulfonyl) trans-1,2-diaminomethyl-cyclopropane 12 (1.4 g, 5.2 mmol (obtained from trans-1,2-diaminomethyl cyclopropane following a previously described mesitylation procedure, see Reddy et al (1998) J. Med. Chem. 41, 4723)) was dissolved in dry DMF (50 ml) under nitrogen, and NaH (60%, 0.4 g) was added to the solution. Stirring was started and after 10 min at 22° C., 1,4-dibromobutane (6.7 g, 31 mmol) dissolved in 25 ml of dry DMF was added in one portion. After stirring the solution for a further 18 h, water was added (5 ml), and the reaction mixture was evaporated to dryness. The residue was purified by column chromatography on silica using hexane/ethyl acetate (4/1) as eluant; 1.5 g (68% yield) of 15 were obtained; ¹H-NMR (CDCl₃) δ: 0.41 (t, J=6.9 Hz, 2H), 0.82 (t, J=6.0 Hz, 2H), 1.66 (m, 8H), 2.29 (s, 6H), 2.58 (s, 12H), 2.94 (m, 2H), 3.21 (m, 10H), 6.94 (s, 4H); ¹³C-NMR (CDCl₃) δ: 11.04, 16.14, 20.93, 22,74, 25.70, 29.65, 32.88, 44.74, 48.88, 131.97, 160.12, 142.48; MS-MALDI (m/z): 757.09 (M⁺+Na).

3,8,13,18,23,28,33,38,43,48-Decakis(mesitylenesulfonyl)-10,11-25,26-40,41-ter[(E)-1,2-cyclopropyl]-3,8,13,23,28,33,38,43,48-decaazapentacontane 16

Tetramide 14 (1.4 g, 1.4 mmol) was dissolved in 50 ml dry DMF and while kept under argon, NaH (60%, 75 mg) was added and the mixture was stirred for 10 min at 22° C. A solution of the dibromo derivative 15 (0.5 g, 0.7 mmol) in 25 ml of dry DMF was then added, and the mixture was stirred for 18 h at 22° C. Water (5 ml) was then added, the solution adjusted to pH 7 with dilute HCl, evaporated to dryness in vacuo, and the residue purified by column chromatography on silica gel using chloroform/ethyl acetate (9:1) as eluant; 1.0 g (28%) of 16 were obtained; ¹H-NMR (CDCl₃) δ: 0.29 (m, 6H), 0.70 (m, 6H), 0.96 (t, J=6.98 Hz, 6H), 1.26 (m, 24H), 2.28 (s, 30H), 2.53, 2.54, 2.55 (s,s,s, 60H), 2.72 (m, 6H), 3.09 (m, 34H), 6.91 (s, 20H); 13C-NMR (CDCl₃) δ: 11.03, 12.73, 15.88, 20.93, 22.72, 24.39, 40.07, 44.61, 44.89, 48.89, 48.72, 131.95, 133.27, 140.04, 142.34; MS-MALDI (m/z) 2594.1 (M⁺+Na).

SL-11232 decahydrochloride 17

10,11-25,26-40,41-ter[(E)-1,2-cyclopropyl]-3,8,13,23,28,33,38,43,48-decaazapentacontane decahydrochloride 17

Decamide 16 (1.0 g) was deprotected with hydrogen bromide (33%) in glacial acetic acid in the presence of phenol following published procedures (Reddy et al (1998) J. Med. Chem. 41, 4723). After treatment with HCl, decahydrochloride 17 was obtained in 80% yield (0.3 g); ¹H-NMR (D₂O) δ: 0.85 (t, 6.9 Hz, 6H), 1.23 (t, J=6.9 Hz, 6H), 1.28 (t, J=7.22 Hz, 6H), 1.78 (m, 24H), 2.89 (m, 6H), 3.10 (m, 34H); ¹³C-NMR (D2O) δ: 12.65, 13.10, 16.28, 25.43, 45.51, 48.86, 49.21, 49.53, 53.28; MS-ESI (m/z) 750 (M⁺+1).

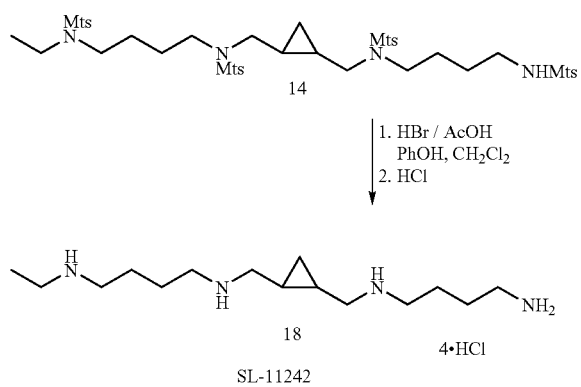

SL-11242 tetrahydrochloride 18

Tetramide 14 (1 g) was dissolved in 10 ml of dry $CH_2Cl_2$, and phenol (2.4 g) was added followed by 13 ml of hydrobromic acid (33%) in glacial acetic acid. Work up followed established procedures (Reddy et al., loc. cit); 230 mg (85%) of 18 were obtained; $^1$H-NMR ($D_2O$) δ: 0.85 (m, 2H), 1.24 (m, 5H), 1.77 (m, 8H), 2.91 (m, 2H), 3.10 (m, 14H); MS-ESI (m/z): 271.2 ($M^+$+1).

Example 4

Synthesis of SL-11241

3,8,13,18,23,28,33,38,43,48-Decakis(mesitylenesulfonyl)-25,26[(E) -1,2-cyclopropyl]-3,8,13,23,28,33,38,43,48-decaazapentacontane 24

Pentamide 23 (6.5 g, 5.25 mmol; prepared as described in International Patent Application WO 00/66587, "Conformationally restricted polyamine analogs as disease therapies") was dissolved in 75 ml of dry DMF, and NaH (60%, 0.32 g) was added in several portions with constant stirring at 22° C. After 10 min, diester 22 (1.2 g, 2.6 mmol; prepared as described in Reddy et al (1998) loc. cit) dissolved in 45 ml of dry DMF was slowly added to the stirred solution and the latter kept for 18 h at 22° C. Water (5 ml) was added, the solution adjusted to pH 7 with dil. HCl, evaporated to dryness, the residue partitioned between $CHCl_3$ (200 ml) and water (100 ml), the organic layer was separated, washed with water (2×100 ml), and evaporated to dryness. The decamide 24 was purified by column chromatography on silica gel using hexane/ethyl acetate (7/3) as eluant; 3.0 g (23%); $^1$H-NMR ($CDCl_3$) d: 0.30 (t, 2H), 0.70 (t, 2H), 0.98 (t, J=7.0 Hz, 6H), 1.27 (m, 32H), 2.30 (s, 30H), 2.55 (s, 60H), 3.0 (m, 40H), 6.93 (s, 20H); $^{13}$C-NMR ($CDCl_3$) δ: 11.04, 12.25, 15.94, 20.93, 22.73, 24.39, 24.78, 40.08, 44.63, 45.19, 48.74, 131.94, 133.26, 140.07, 142.32; MS-MALDI (m/z): 2567 ($M^+$+Na).

SL-11241 decahydrochloride 25

Decamide 24 (1 g) was deprotected using hydrogen bromide (33%) in glacial acetic acid in the presence of phenol as described elsewhere (Reddy et al (1998) loc cit). Treatment with HCl gave decahydrochloride 25 in 85%

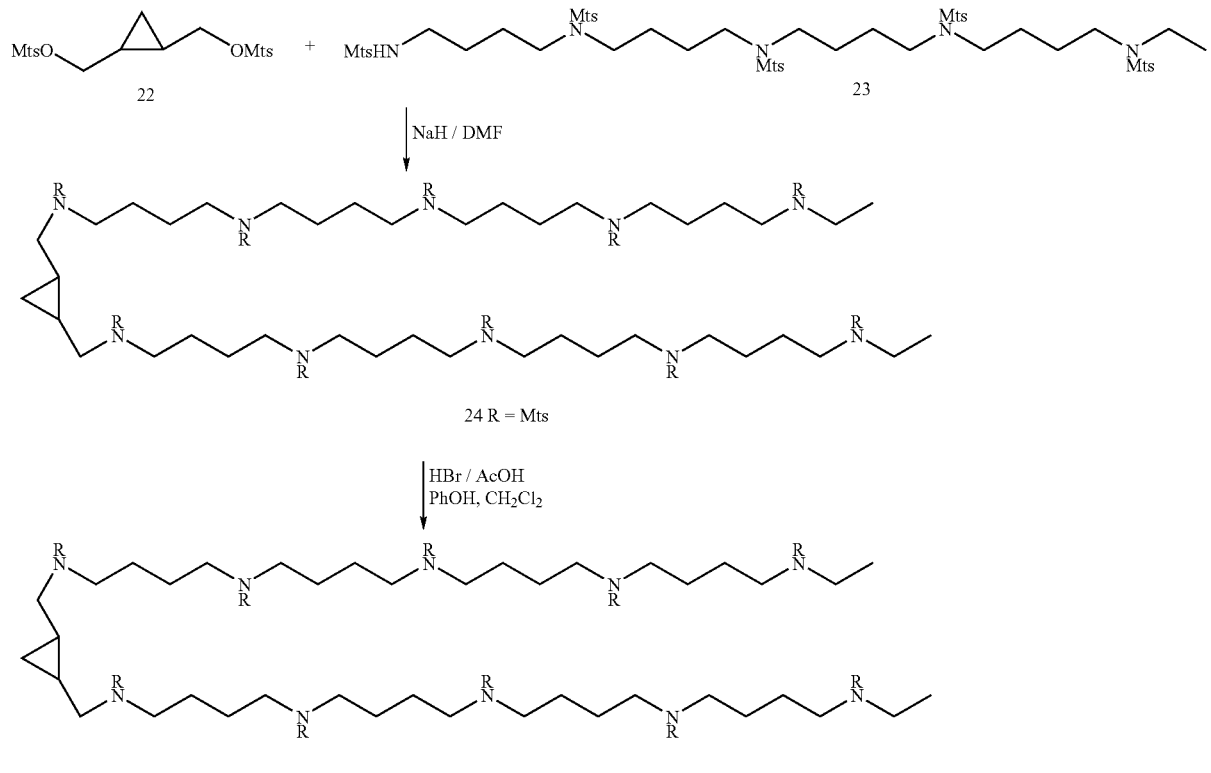

yield. $^1$H-NMR (D$_2$O) δ: 0.88 (t, J=7.10 Hz 2H), 1.20 (t, J=7.10 Hz, 2H), 1.28 (t, J=7.13 Hz, 6H), 1.78 (m, 32H), 3.10 (m 40H); MS (m/z): 725.8 (M$^+$+1).

Example 5

Synthesis of SL-11245 and SL-11247

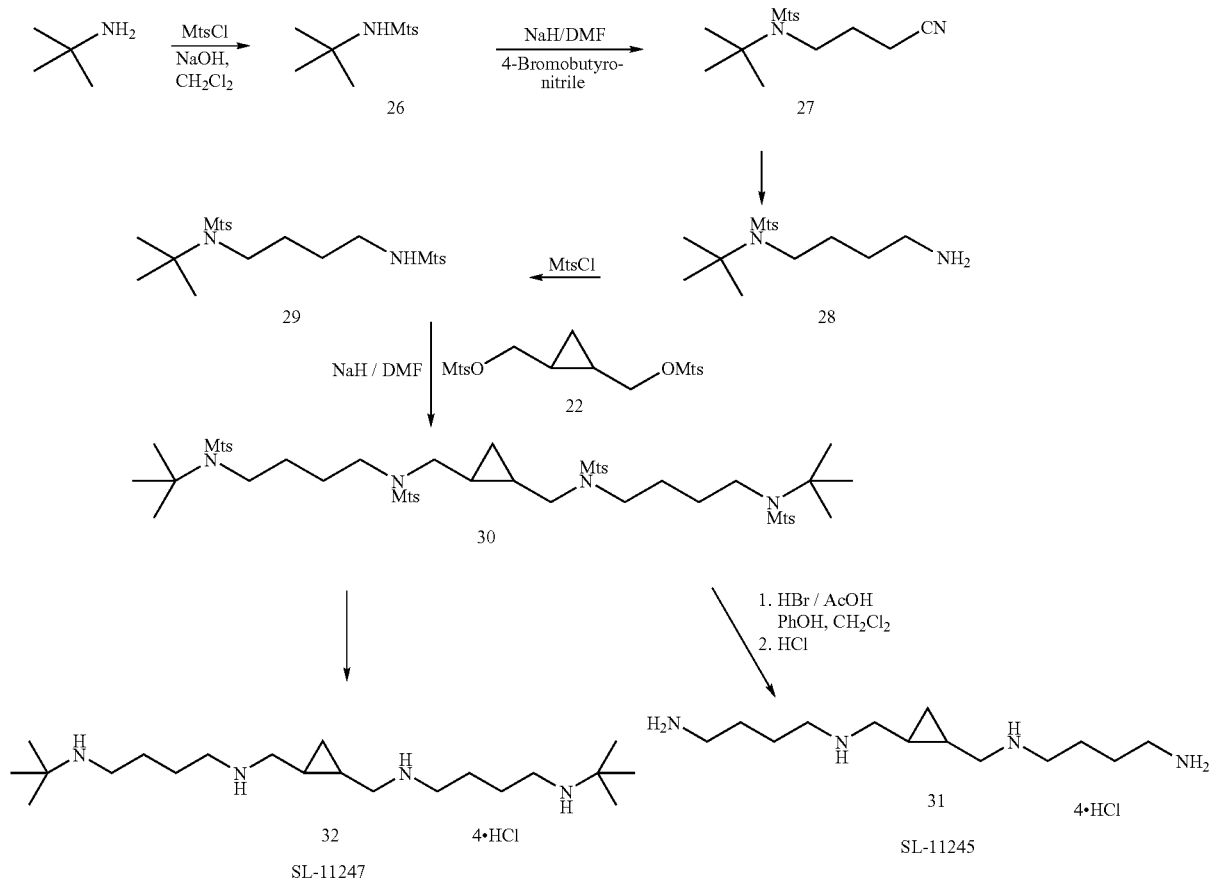

tert-Butyl(mesitylene sulfonyl) amide 26 t-Butylamine (4.3 ml, 41 mmol) was dissolved in 50 ml of methylene chloride and 75 ml of 4% sodium hydroxide. The solution was cooled to 5° C., and mesitylenesulfonyl chloride (11.7 g, 53.3 mmol) dissolved in 75 ml of methylene chloride was slowly added over 1 h. The mixture was stirred at 5° C. for 3 h and then at 22° C. for 18 h. The organic layer was then separated, the aqueous layer extracted with 30 ml of methylene chloride, the organic layers were combined, dried (MgSO4), evaporated to dryness, and the residue was recrystallized from hexane/ethyl acetate; 6.0 g (57%) of 26 were obtained; mp 149–150° C.; $^1$H-NMR (CDCl$_3$) δ: 1.21(s, 9H), 2.29 (s, 3H), 2.66 (s, 6H), 4.68 (br, 1H), 6.94 (s, 2H); $^{13}$C-NMR (CDCl$_3$) δ:20.83, 22.84, 29.99, 54.47, 131.95, 138.26, 141.53.

N,N-t-butyl(mesitylensulfonyl)-4-aminobutyronitrile 27

Amide 26 (2.55 g, 10 mmol) was dissolved in dry DMF (30 ml) under an argon atmosphere, and NaH (60%, 0.5 g) was added at 22° C. The mixture was stirred for 30 min, and 4-bromobutyronitrile (1.6 g, 11 mmol) dissolved in 10 ml of dry DMF were then added. The mixture was kept at 22° C. for 18 h, the DMF was evaporated in vacuo, and the residue was partitioned between ethyl acetate (30 ml) and water (30 ml). The organic layer was separated, evaporated to dryness, and the oily residue was purified by chromatography on silica gel using hexane/ethyl acetate (7/3) as eluant; 1.7 g (52%) of the nitrile 27 were recovered; mp 82° C.; $^1$H-NMR (CDCl$_3$) δ: 1.32 (s, 9H); 2.02 (m, 2H), 2.29(s, 3H), 2.36 (t, J=7.17 Hz, 2H), 2.60 (s, 6H), 3.48 (dd, J=7.68, 7.86 Hz, 2H), 6.93 (s, 2H); $^{13}$C-NMR (CDCl$_3$) δ: 15.01, 20.81, 22.85, 27.27, 29.70, 45.12, 59.45, 118.97, 132.19, 138, 142.04.

$^1$N,$^4$N-(bis-mesitylenesulfonyl)-N-t-butyl-1,4-diaminobutane 29

Nitrile 27 (1.6 g, 5 mmol) dissolved in 15 ml of methanol and 15 ml of chloroform was reduced with hydrogen at 50 psi over platinum oxide (0.18 g) during 18 h. The catalyst was separated, the solvent evaporated to dryness and the residue (1.7 g of 28) was used in the next step without further purification. It was dissolved in a mixture of 20 ml methylene chloride and 10 ml 8% sodium hydroxide, and mesitylenesulfonyl chloride (1.4 g, 6 mmol) dissolved in 20 ml of methylene chloride were slowly added. The mixture was stirred for 18 h at 22° C., the organic layer was separated, the aqueous layer washed with 20 ml of methylene chloride, the combined organic layers were evaporated to dryness, and the residue was purified by chromatography on silica gel using hexane/ethyl acetate (7/3) as eluant; 1.4 g (50%) of 29 were obtained; mp 157° C.; $^1$H-NMR (CDCl$_3$) δ: 1.28 (s, 9H), 1.38(m, 2H), 1.57 (m, 2H), 2.28 (s, 3H), 2.30 (s, 3H), 2.57 (s, 6H), 2.63(s, 6H), 2.83 (q, J=6.61 Hz, 2H), 3.25(dd, J=7.60, 8.08 Hz, 2H), 4.58 (t, 1H), 6.90 (s, 2H), 6.96 (s, 2H); $^{13}$C-NMR (CDCl$_3$) δ: 20.83, 22.88, 27.19, 28.70, 29.83, 42.03, 45.76, 59.19, 131.97, 132.06, 138.92, 141.0.

1,13-(bis(t-butyl)mesitylenesulfonylamide)-[(E)-7,8-cyclopropyl]-5,10-bis(mesitylenesulfonyl)-5,10-diazatridecane 30

Diamide 29 (1.35 g, 2.7 mmol) and diester 22 (0.6 g, 1.3 mmol, prepared as described in Reddy et al (1998) loc. cit.) were dissolved in dry DMF (20 ml) under argon, and NaH (60%, 0.14 g) were added. The mixture was stirred for 18 h at 22° C., the solvent distilled off in vacuo, the residue partitioned between 30 ml ethyl acetate and 20 ml of water, the organic layer was separated, evaporated to dryness, and the residue purified by column chromatography on silica gel using hexane/ethyl acetate (7/3) as eluant; 0.8 g (54%) of 30 were obtained; $^1$H-NMR (CDCl$_3$) δ: 0.39 (t, 2H), 0.78 (t, 2H), 1.26 (s, 18H), 1.36 (m, 8H), 2.28 (s, 6H), 2.30 (s, 6H), 2.57 (s, 24H), 2.89 (m, 2H), 3.19 (m, 10H), 6.89 (s, 4H), 6.94 (s, 4H); $^{13}$C-NMR (CDCl$_3$) δ: 16.02, 20.85, 22.89, 24.92, 28.88, 29.84, 45.33, 45.97, 48.76, 59.17, 131.99, 138.93, 140.11, 141.68, 142.37; MS-MALDI (m/z) 1105.57 (M$^+$+Na).

SL-11245 tetrahydrochloride 31

Tetramine 31 was obtained by deprotecting 30 following the procedure described in Reddy et al (1998) J. Med. Chem. 41, 4723. Yield of 31 was 63%; $^1$H-NMR (D$_2$O) δ: 0.85 (t, J=6.77 Hz, 2H), 1.34 (t, J=6.99 Hz, 2H), 2.03 (m, 8H), 3.31 (m, 4H), 3.44 (m, 8H); $^{13}$C-NMR (D$_2$O) δ: 17.23, 24.38, 30.91, 32.42, 36.75; MS-ESI (m/z) 243.2 (M$^+$+1).

SL-11247 tetrahydrochloride 32

Tetrahydrochloride 32 was obtained from tetramide 30 by deprotection in alkaline medium using sodium in liquid ammonia following the procedure described by Bergeron et al. (1994) J. Med. Chem. 37, 3464; yield was 10%; $^1$H-NMR (CDCl$_3$) δ: 0.86 (m, 2H), 1.23 (M, 2H), 1.37 (s, 18H), 1.77 (m, 8H), 2.88 (m, 2H), 3.10 (m, 10H).

Example 6

Synthesis of SL-11215 and SL-11218

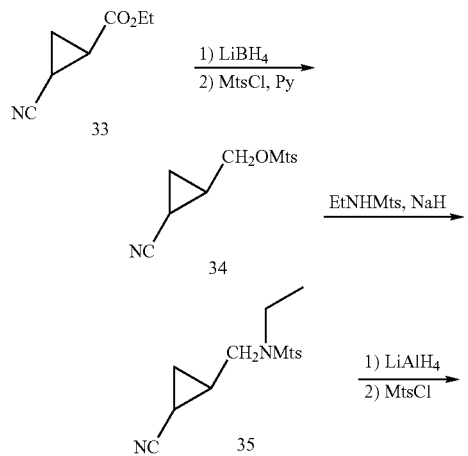

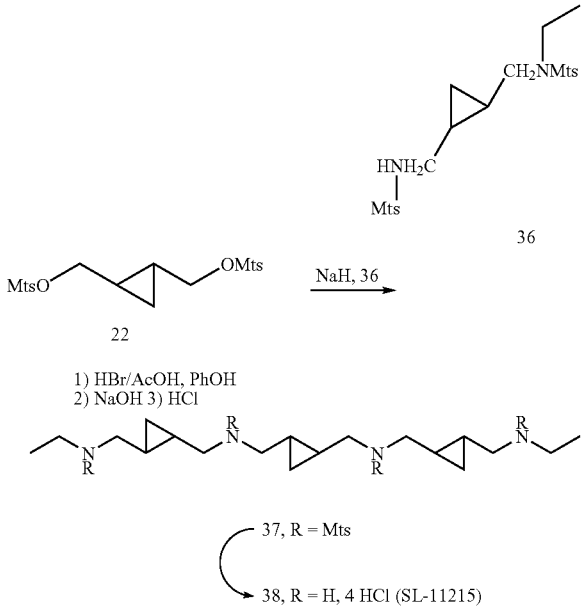

trans-1-cyano-2(mesitylenesulfonyloxymethyl)-cyclopropane 34

A solution of ethyl (E)-2-cyanocyclopropanecarboxylate 33 (Ashton et al., J. Med. Chem. 1988, 31, 2304) (8 g, 57.5 mmol) in isopropyl alcohol (8 mL) was added over 5 min into an ice cold N$_2$ swept solution of LiBH$_4$ (1.254 g, 57.5 mmol) in isopropyl alcohol (40 mL). The reaction mixture was stirred for 0.5 h in an ice bath, the bath was removed and the reaction was continued at RT for another 3 h. The reaction mixture was concentrated in vacuo and evaporated three times from toluene. Et$_2$O (130 mL) and H$_2$O (2.5 mL) were added and the reaction mixture was stirred for 10 h at RT. It was dried with Na$_2$SO$_4$, filtered, and concentrated on a rotary evaporator. The residue, the crude 2-cyano-1-hydroxymethylcyclopropane was dissolved in pyridine (50 mL), cooled to 0° C. and mesitylenesulfonyl chloride (18.88 g, 86.34 mmol) in pyridine (60 mL) was slowly added into the reaction mixture. Following 3 h of stirring at RT the reaction mixture was poured on ice (500 g), acidified with 10% HCl, and the product 34 was extracted with ethyl acetate. It was purified by washing with solutions of 3% HCl, NaHCO$_3$, and brine, followed by column chromatography (silica gel, hexane/ethyl acetate, 4:1). Yield 5.25 g (33%); $^1$H-NMR (CDCl$_3$) δ 0.8–1.1 (m, 1H), 1.25–1.40 (m, 2H), 1.70–1.90 (m, 1H), 2.33 (s, 3H), 2.63 (s, 6H), 3.80 (dd, J$^1$=11.2 Hz, J$^2$=7.2 Hz, 1H), 4.03 (dd, J$^1$=11.2 Hz, J$^2$=5.9 Hz, 1H, 1H), 7.00 (s, 2H); $^{13}$C-NMR (CDCl$_3$) δ 2.28, 11.75, 19.35, 21.01, 22.53, 69.26, 119.90, 126.35, 131.88, 139.82, 143.75; MS-ESI (m/z) 280.2 (M$^+$+1).

N-(1-Cyanocyclopropylmethyl)-N-ethyl mesitylenesulfonamide 35

A suspension of NaH (508 mg, 60% in mineral oil, 12.7 mmol) in DMF (15 mL) was added to a stirred solution of 34 (2.33 g, 8.34 mmol) and N-ethylmesitylenesulfonamide (2.116 g, 9.32 mmol) at 5° C. and the mixture stirred for 1 h. The cooling bath was removed, and the reaction mixture was left stirring for an additional 10 h. After the mixture was cooled in an ice bath, it was quenched with H$_2$O, neutralized to pH=7 with 2% HCl, concentrated on a rotary evaporator, suspended in CHCl$_3$ and washed 2 times with H$_2$O and brine. Column purification (silica gel, hexane:EtOAc=4:1) yielded 2.42 g (95%) of the product 35; $^1$H NMR (CDCl$_3$) δ 0.85–1.00 (m, 1H), 1.1 (t, 3H), 1.20–1.30 (m, 1H), 1.60–1.75 (m, 1H), 2.31 (s, 3H), 2.59 (s, 6H), 3.06–3.26 (m, 2H), 3.25–3.34 (m, 2H), 7.00 (s, 2H); $^{13}$C NMR (CDCl$_3$) δ 2.75, 12.76, 12.98, 19.66, 20.88, 22.62, 41.06, 47.43, 120.62, 132.03, 132.63, 140.21, 142.76; MS-ESI (m/z) 307.4 (M$^+$+1).

N-Ethyl N,N'-bis(mesitylenesulfonyl)-trans-1,2-bis(aminomethylcyclopropane) 36

A solution of nitrile 35 (2.42 g, 7.91 mmol) in Et$_2$O (50 mL) was slowly added into a stirred suspension of LiAlH$_4$ (368 mg, 9.68 mmol) in Et$_2$O (10 mL) at 0° C., the mixture stirred for 2.5 h, the cooling bath removed and the reaction mixture was left stirring for 20 h at 23° C. The reaction mixture was quenched with 2N NaOH at 0° C., the inorganic precipitate was filtered and washed through with Et$_2$O. The Et$_2$O solution was dried (Na$_2$SO$_4$) and concentrated in vacuo. The residue was dissolved in CH$_2$Cl$_2$ (30 mL), mesitylenesulfonyl chloride (1.684 g, 7.7 mmol) was added, the reaction mixture was cooled on an ice bath and treated with sodium hydroxide (2N, 16 mL). After 4 h the reaction mixture was quenched with H$_2$O (60 mL), acidified to pH=1, the product was extracted with CHCl$_3$, washed with brine, dried (Na$_2$SO$_4$) and purified on a silica gel column (hexane: EtOAc=4:1). Yield 1.69 g (43%). $^1$H NMR (CDCl$_3$) δ 0.40–0.52 (m, 2H), 0.94 (t, 3H), 0.95–1.15 (m, 2H), 2.29 (s, 3H), 2.30 (s, 3H), 2.40–2.52 (m, 1H), 2.57 (s, 6H) 2.59 (s, 6H), 2.90–3.45 (m, 5H), 5.58 (t, 1H), 6.94 (4H); $^{13}$C NMR (CDCl$_3$) δ 10.10, 12.33, 16.45, 17.51, 20.87, 20.93, 22.55, 22.93, 40.01, 46.61, 47.71, 131.81, 131.88, 132.49, 133.96, 139.08, 140.39, 141.75, 142.52; MS-ESI (m/z) 493.4 (M$^+$+1).

3,8,13,18-Tetrakis(mesitylenesulfonyl)-ter[(E)-5,6,(E)-10,11,(E)-15,16-cyclopropyl]-3,8,13,18-tetrazaeicosane 37

Sodium hydride (60% suspension in oil, 161 mg, 3, 3.97 mmol) was added to a stirred mixture of diester 22 (676 mg, 1.45 mmol, prepared as described in Reddy et al. (1998) loc. cit) and diamide 36 (1.456 g, 2.95 mmol) in dry DMF (12 mL) at 0° C. The cooling bath was removed and the stirring was continued for 10 h. The reaction mixture was quenched with water (1 mL), acidified to pH=6 with aq. HCl (3%), and concentrated to dryness in vacuo at 40° C. The residue was dissolved in EtOAc, washed with water (3 times), brine, and dried (Na$_2$SO$_4$). Column chromatography (silica gel, hexane:EtOAc=3:1) yielded tetrasulfonamide 37; 1.26 g (83%). $^1$H NMR (CDCl$_3$): 0.25–0.50 (m, 6H), 0.70–0.95 (m, 6H), 0.95–1.10 (m, 6H), 2.29 (s, 12H), 2.55 (s, 24H), 2.85–3.10 (m, 6H), 3.10–3.40 (m, 10H), 6.92 (s, 8H). $^{13}$C NMR (CDCl$_3$): 10.92, 11.15, 12.64, 16.00. 16.16, 16.32, 20.92, 22.67, 40.26, 48.41, 49.04 49.22, 131.88, 133.23, 133.36, 140.16, 142.21, 142.32. MS-MALDI (m/z) 1073.6 (M$^+$+Na).

SL-11215 tetrahydrochloride 38

Tetrasulfonamide 37 (1.26 g, 1.2 mmol) was stirred for 10 h in a mixture of phenol (4.5 g, 48 mmol), HBr (33% in AcOH, 26 mL), and CH$_2$Cl$_2$ (13 mL). The mixture was cooled in an ice bath, quenched with water (5.5 mL), washed 2 times with CH$_2$Cl$_2$, and concentrated in vacuo. The residue was neutralized with 2N NaOH (1 mL) at 0°, then basified with KOH (50%, 1 mL) to pH=12, extracted with CHCl$_3$ (5 times), dried (Na$_2$SO$_4$), and concentrated in vacuo. The residue was dissolved in Et$_2$O and precipitated with HCl gas. The product was filtered, washed with Et$_2$O and dried in vacuo. Yield 374 mg (66%); mp: above 200° (decomp.). $^1$H NMR (D$_2$O): 0.80–0.92 (m, 6H), 1.15–1.85 (m, 6H), 1.29 (t, J=7.3, 6H), 6.28–3.00 (m, 6H), 3.12 (q, J=7.3, 4H), 3.10–3.35 (m, 6H). $^{13}$C NMR (D$_2$O): 10.03, 10.14, 10.60, 13.78, 42.69, 50.13, 50.45. MS-ESI (m/z) 323.2 (M$^+$+1).

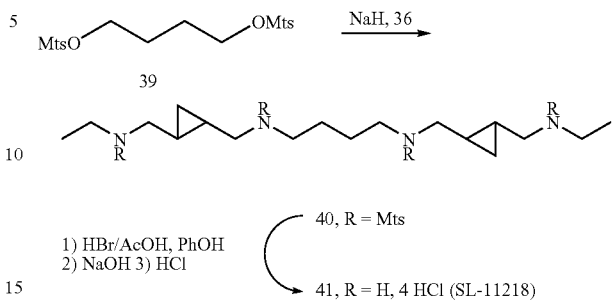

SL-11218 tetrahydrochloride 41

Analogously to the procedure described above for obtaining 37, the tetrasulfonamide 40 was prepared by condensation of the diester 39 and the amide 36 in 93% yield. $^1$H NMR (CDCl$_3$): 0.25–0.45 (m, 4H), 0.65–0.85 (m, 4H), 0.99 (t, J=7.1, 6H), 1.30–1.42 (m, 4H), 2.29 (s, 12 H), 2.56 (s, 24 H), 2.55–2.95 (m, 4H), 3.05–3.35 (m, 12H), 6.92 (s, 8H). $^{13}$C NMR (CDCl$_3$): 10.88, 12.65, 15.99, 16.22, 20.91, 22.67, 22.71, 24.42, 40.30, 45.24, 48.41, 48.78, 131.90, 133.33, 140.10, 142.23, 142.30. MS-MALDI 1061.5 (M$^+$+Na).

Treatment of 40 with HBr/AcOH in the presence of phenol as described for 37 gave 41 (71%). mp.: above 200° C. (dec); $^1$H NMR (D$_2$O) δ: 0.85 (t, J=7.1, 4H), 1.15–1.30 (m, 4H), 1.26 (t, J=7.4, 6H), 1.75–1.90 (m, 4H), 2.82–3.00 (m, 4H), 3.05–3.30 (m, 12H); $^{13}$C NMR (D$_2$O) δ: 10.00, 10.60, 13.75, 22.89, 42.68, 46.65, 50.12, 50.74; MS-ESI: 311.4 (M$^+$+1).

Example 7

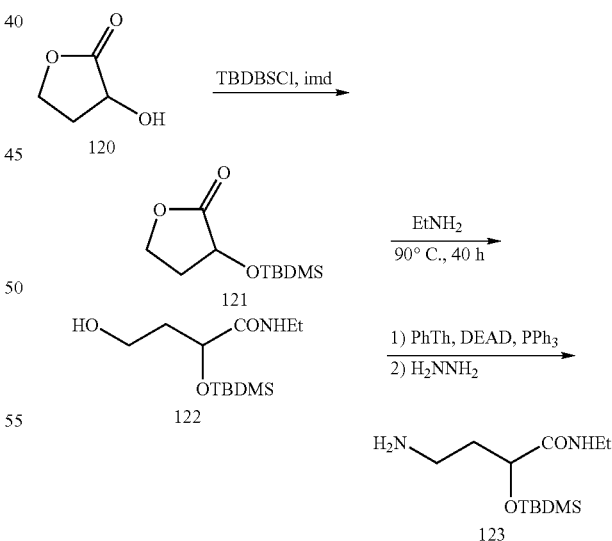

Preparation of hydroxyalkyl segments. 2-Hydroxy-γ-butyrolactone 120 was used as a starting material. (This compound is commercially available as both R and S isomers.) Following the protection of hydroxy group with t-butyldimethylsilyl chloride (TBDMSCl), the resulting lactone 121 was treated with a THF solution of EtNH$_2$. The resulting hydroxy amide 122 was subjected to a Mitsunobu reaction with phthalimide (PhTh), diethylazodicarboxylate (DEAD), and triphenylphosphine, followed by deprotection with hydrazine to obtain amine 123.

The resulting amino group can be protected with mesitylenesulfonyl chloride and used in a manner analogous to the amine segments above to introduce hydroxyalkyl segments into the polyamine analog as desired. The amide group can be reduced to an amino group via treatment with $BH_3$-THF reagent, or lithium aluminum hydride.

Example 8

The polyamine analogs inhibited prostate cancer cell growth in vitro., as indicated in Table 1 and FIG. 1, FIG. 2, FIG. 3, FIG. 4, and FIG. 5. Tissue cultures and the MTT assay were performed as follows. Additional protocols for in vitro assays are dislosed in International Patent Applications WO 00/66175, WO 00/66528, WO 00/66587, WO 98/17624, Valasinas et al., J. Med. Chem. 44:390–403 (2001), and United States Provisional Patent Application Serial No. 60/329,982 filed Oct. 16, 2001.

Tissue Culture. Cells were seeded into 75 $cm^2$ culture flasks with 15 ml of Eagle's minimal essential medium supplemented with 10% fetal calf serum and nonessential amino acids. The flasks were incubated in a humidified 95% air/5% $CO_2$ atmosphere. The cells were grown for at least 24 h to ensure that they are in the log phase of growth and then they were treated with the polyamine analogs. Cells were harvested by treatment for 5 min with STV (saline A, 0.05% trypsin, 0.02% EDTA) at 37° C. The flasks were rapped on the lab bench, pipetted several times and aliquots of cell suspension were withdrawn and counted using a Coulter particle counter that has been standardized for counting each cell line using a hemacytometer.

MTT Assay: Trypsinized cell suspensions were diluted to seed 80 µl suspensions containing 500 cells in each well of a 96 well Corning microtiter plate and incubated overnight at 37° C. in a humidified incubator in 5% $CO_2$. 20 µl of appropriately diluted stock solution of each drug (i.e., polyamine analog) were added to the middle 8 columns of cell suspension in the microtiter plates. Each drug concentration was run in quadruplicate. Outer columns of the plates were used for buffer controls. Cells were incubated with the drug for 6 days at 37° C. in 5% $CO_2/H_2O$ atmosphere. 25 µl of 5 mg/ml solution of 3-(4,5-dimethylthiazol-2-yl)-2,5-diphenyl tetrazolium bromide (MTT) were added to each well and incubated for 4 hours at 37° C. in 5% $CO_2/H_2O$ incubator. Cells were lysed by incubating overnight with 100 µl lysis buffer (500 ml of the lysis buffer contains: 100 g lauryl sulfate (SDS), 250 ml of N,N-dimethylformamide, and 2 ml of glacial acetic acid, made up to volume with water; pH 4.8).

The color was monitored at room temperature at 570 nm in a E-max Precision Microplate Reader (Molecular Devices Corporation, Sunnyvale, Calif.) and data was analyzed using cell survival software supplied by Molecular Devices Corporation.

TABLE 1

| ID50 (µM) values for human prostate cancer cell lines | | | | | | |
|---|---|---|---|---|---|---|
| Compound | DuPro | PC-3 | DU145 | LnCap | Tsu-pr1 | Tsu-pr1-ADR |
| SL-11093 | 0.20 | 4.17 | 0.01 | 0.21 | 0.07 | >31.25 |
| SL-11215 | 0.63 | >31.25 | 0.06 | | | |
| SL-11218 | 0.26 | >31.25 | 0.063 | | | |

TABLE 1-continued

| ID50 (µM) values for human prostate cancer cell lines | | | | | | |
|---|---|---|---|---|---|---|
| Compound | DuPro | PC-3 | DU145 | LnCap | Tsu-pr1 | Tsu-pr1-ADR |
| SL-11231 | 0.38 | >31.25 | 0.08 | 0.15 | | |
| SL-11232 | 0.20 | 0.30 | | | | |
| SL-11241 | 0.34 | 0.40 | 0.20 | | | |
| SL-11242 | | >31.25 | | | | |
| SL-11245 | >31.25 | >31.25 | 0.61 | | | |
| SL-11247 | >31.25 | >31.25 | 11.17 | | | |

Example 9

The effects of SL-11218 and SL-11231 on the growth of human prostate tumor cell lines PC-3, DU-145, DuPro and LnCap and on human breast cancer cell lines MCF-7 and MDA-MB-231 in culture were determined by an MTT assay. The growth inhibitory effects were expressed as $ID_{50}$ value which is defined as the drug concentration required to inhibit 50% cell growth after 5 days of treatment. The results are shown in Table 2; the numbers are the average of the values determined in at least three separate experiments. Both compounds are effective in inhibiting human prostate tumor cell growth in culture. SL-11218 also showed some activity against the MCF-7 breast cancer cells.

TABLE 2

$ID_{50}$ values of cyclopropyl polyamine analogs against human tumor cell lines as determined by a MTT assay

| | $ID_{50}$ (µM) | | | | | |
|---|---|---|---|---|---|---|
| Serial No. | PC3 | DUPRO | DU145 | LnCap | MCF-7 | MDA-MB-231 |
| SL-11218 | >31.25 | 0.26 | 0.06 | ND | 4.25 | >31.25 |
| SL-11231 | >31.25 | 0.38 | 0.12 | 0.15 | >31.25 | >31.25 |

ND = Not determined

Figure 6:
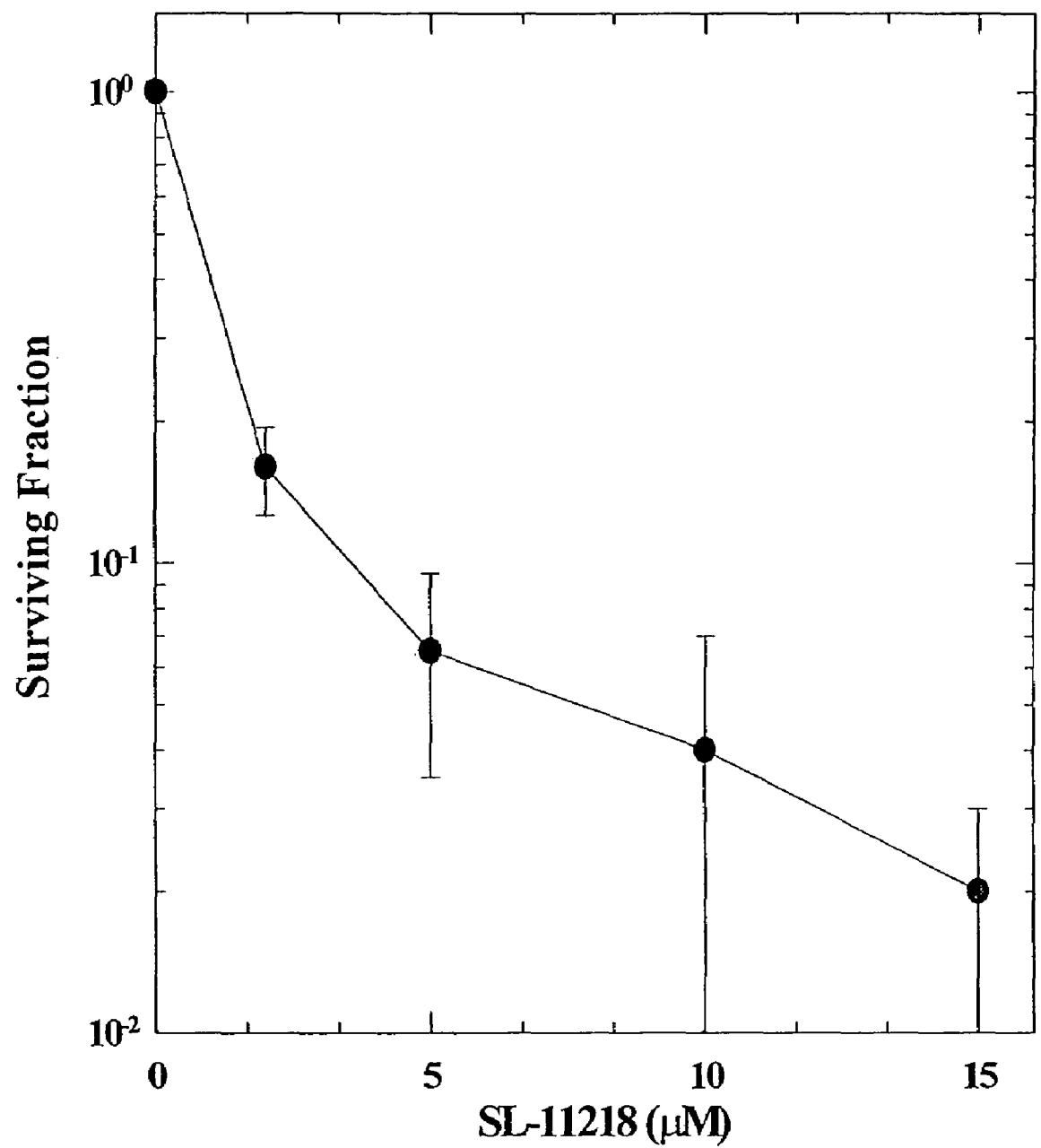
FIG. 6 is a graph depicting the effect of SL-11218 on the human prostate tumor cell line DuPro after 5 days of incubation.

SL-11218 exhibited marked cytotoxicity against DuPro human prostate tumor cell line as determined by a colony forming efficiency (CFE) assay. The CFE data are shown in FIG. 6.

Figure 7A:
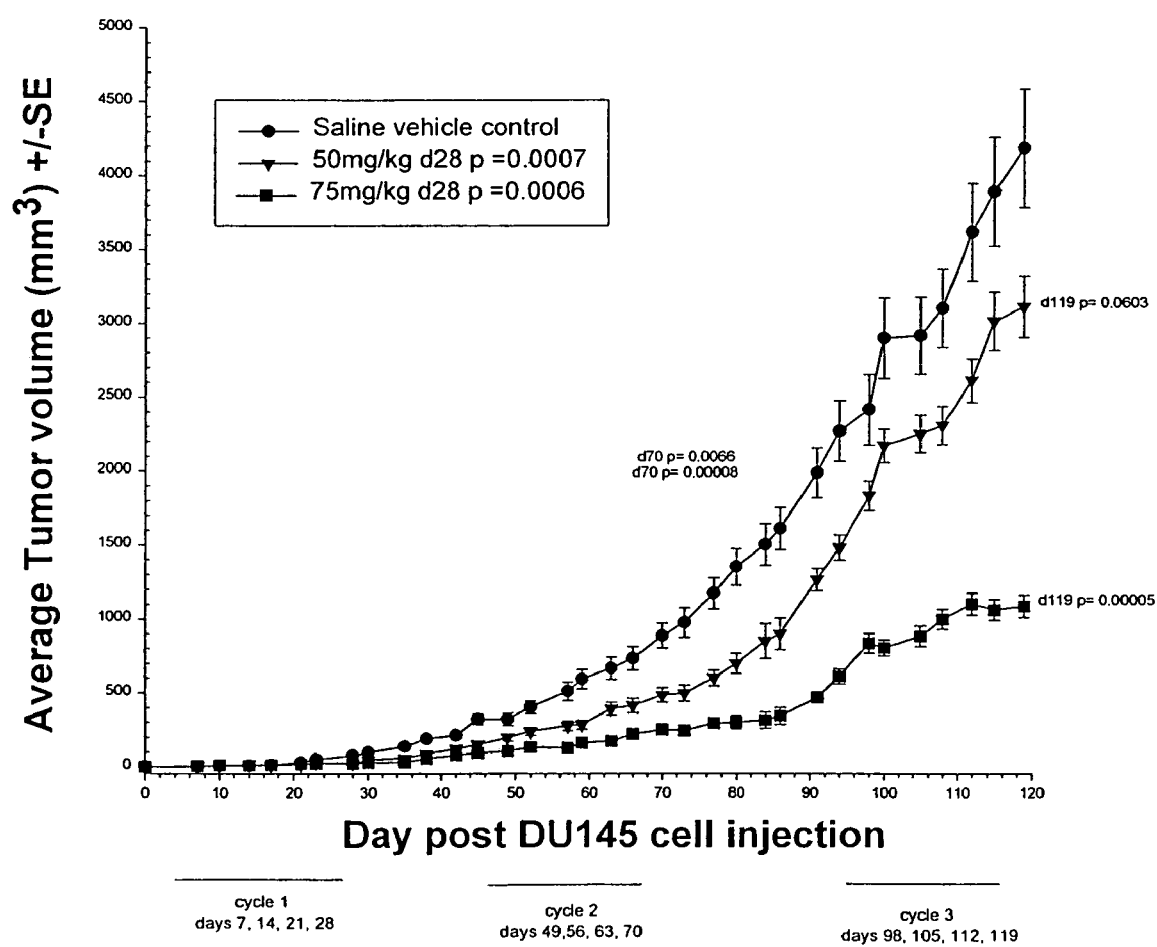
FIG. 7a is a graph depicting the efficacy of SL-11218 against DU145 xenografts (50 or 75 mg/kg i.p. once weekly ×4 q 3 weeks). Circles indicate saline control vehicle, triangles indicate SL-11218 at dosage of 50 mg/kg, squares indicate SL-11218 at dosage of 75 mg/kg.
Figure 7B:
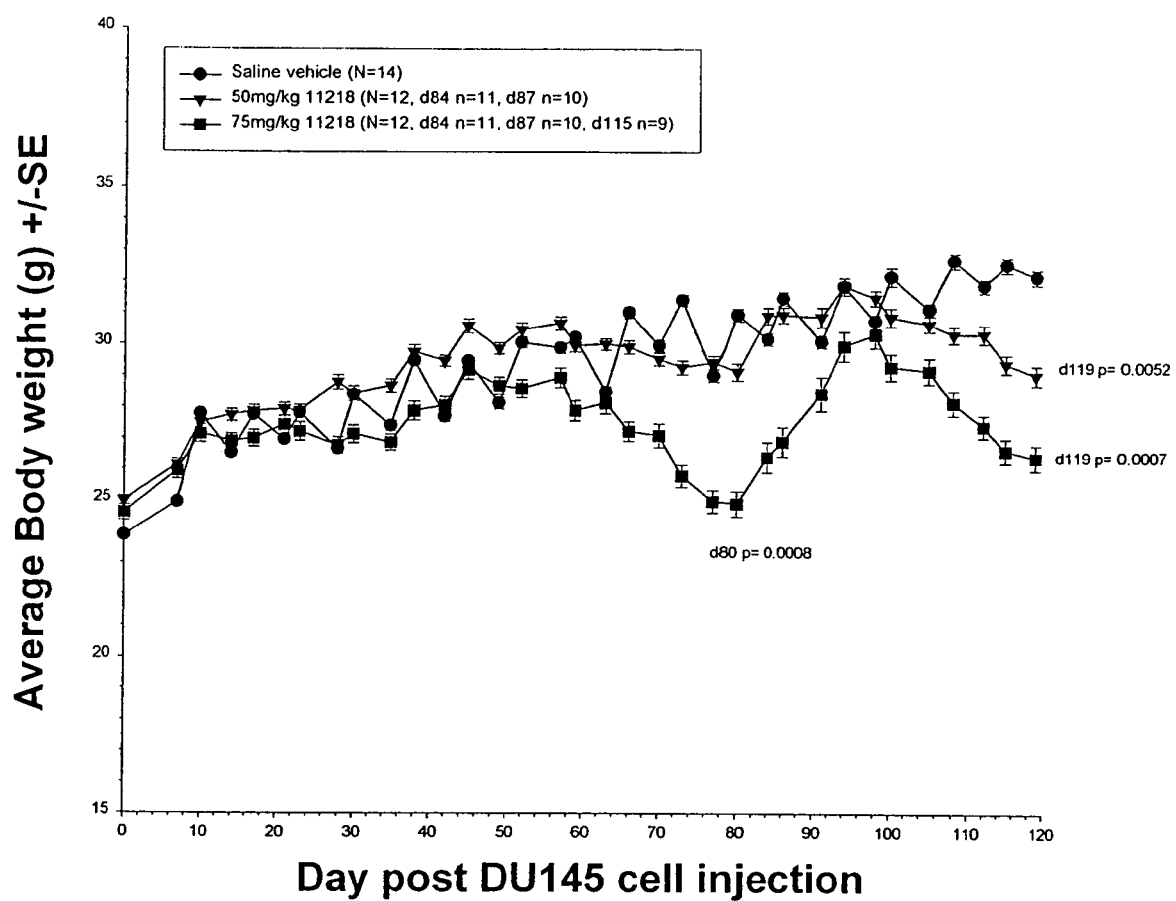
FIG. 7b is a graph depicting the effect of SL-11218 on animal bodyweight. Circles indicate saline control vehicle, triangles indicate SL-11218 at dosage of 50 mg/kg, squares indicate SL-11218 at dosage of 75 mg/kg.

The effect of SL-11218 50 mg/kg and 75 mg/kg against DU-145 human prostate tumor xenograft in nude mice are shown in FIG. 7a. Male athymic nude mice were given s.c. injections of $1 \times 10^6$ DU-145 cells on Day 0. Beginning on Day 7, mice were treated i.p q1w×4 for 3 cycles with either saline, 50 mg/kg SL-11218 or 75 mg/kg SL-11218 (pH 7.4) i.p. at 10 ml/kg dosing volume. (Cage issues in the control cage were due to a water bottle leaking and lack of food for 24 hours.) The treatment was carried out once weekly for four weeks (q1w×4) in 3 cycles with a 4 week gap between each cycle. (i.e., cycle 1, administration on days 7, 14, 21, 28; cycle 2, administration on days 49, 56, 63, 70; cycle 3, administration on days 98, 105, 112, 119). All p values were compared to vehicle treated mice. (At d 28, p=0.0007 for the 50 mg/kg group; p=0.0006 for the 75 mg/kg group; at d70, p=0.0066 and 0.00008 for 50 mg/kg and 75 mg/kg, respectively; at d119, p=0.0603 and 0.00005 for 50 mg/kg and 75 mg/kg, respectively. The body weights of treated animals are also included in FIG. 7b. (For saline vehicle, N=14; for 50 mg/kg group, n=12; at d84, n=11; at d87, n=10; and p=0.0052 at d119; for 75 mg/kg group, n=12; at d84, n=11; at d87, n=10; at d115, n=9; and p=0.0007 at d119.) While 50 mg/kg treatment temporarily arrested tumor growth, 75 mg/kg treatment arrested tumor growth throughout the treatment period of 120 days without appreciable bodyweight loss.

Figure 8B:
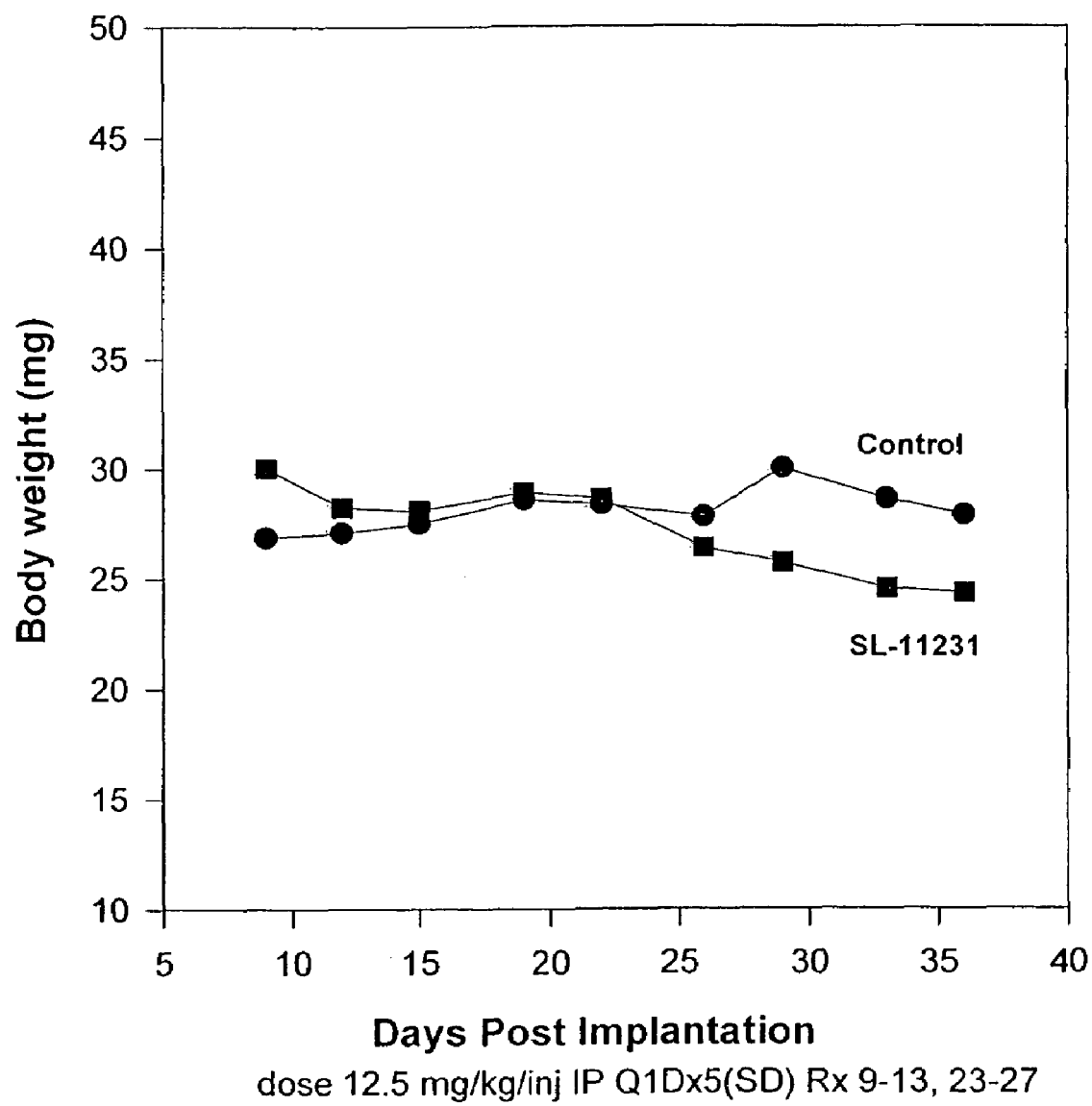
FIG. 8b is a graph depicting the effect of SL-11231 on animal body weight. Circles indicate data for control, squares indicate data for SL-11231.

The effect of SL-11231 at 12.5 mg/kg for 5 consecutive days against DU-145 human prostate tumor xenograft in nude mice is shown in FIG. 8a. At this dose, SL-11231 also efficiently inhibits tumor growth without appreciable effects on animal bodyweight (FIG. 8b). (Note that the value reported in Table 1 for SL-11231 versus DU-145 cells is for a single experiment, while the value reported in Table 2 is an average of multiple experiments.)

Figure 9:
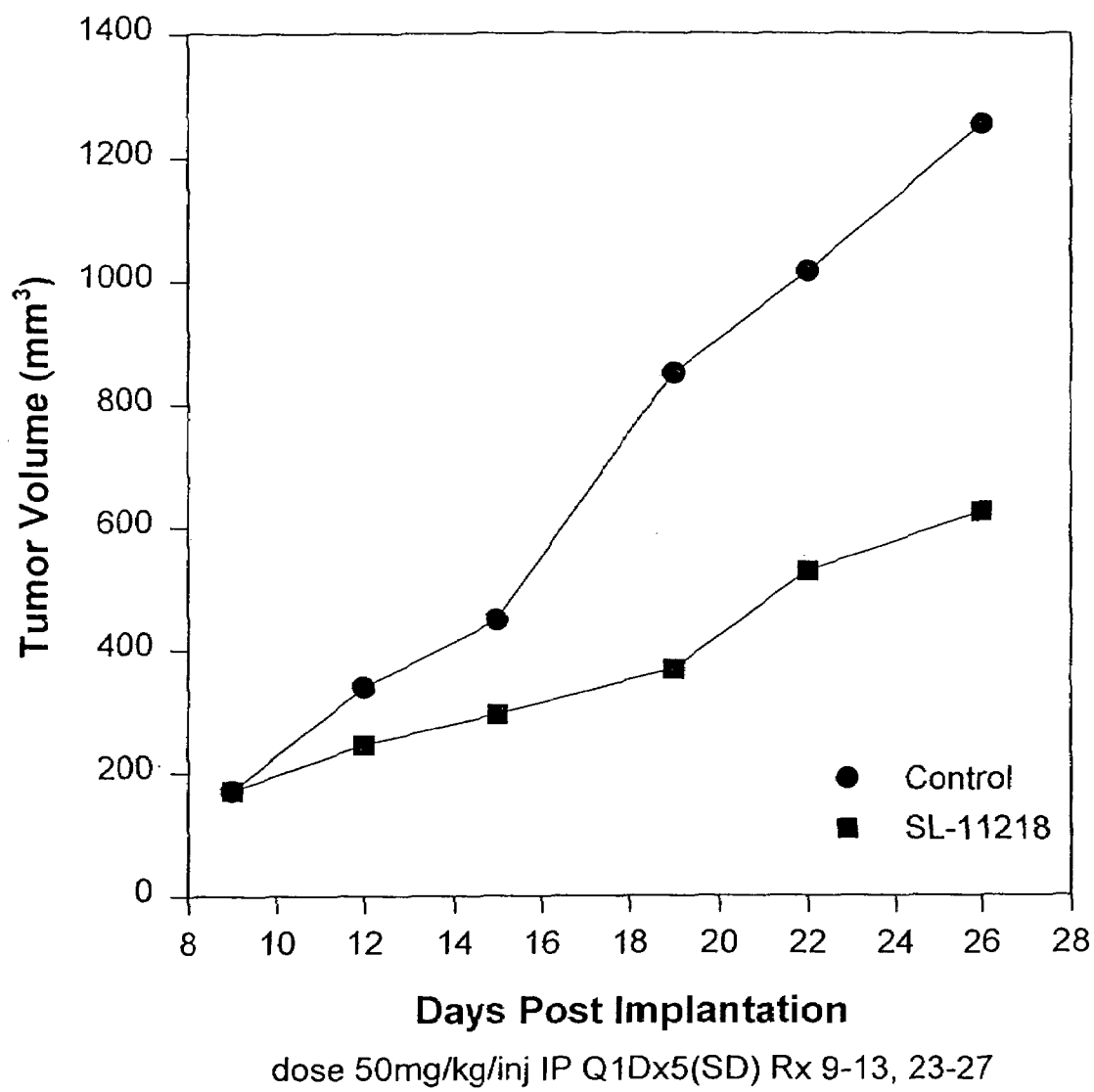
FIG. 9 is a graph depicting the effect of SL-11218 on BxPC-3 human pancreatic tumor volume. Circles indicate data for control, squares indicate data for SL-11218.
Figure 10:
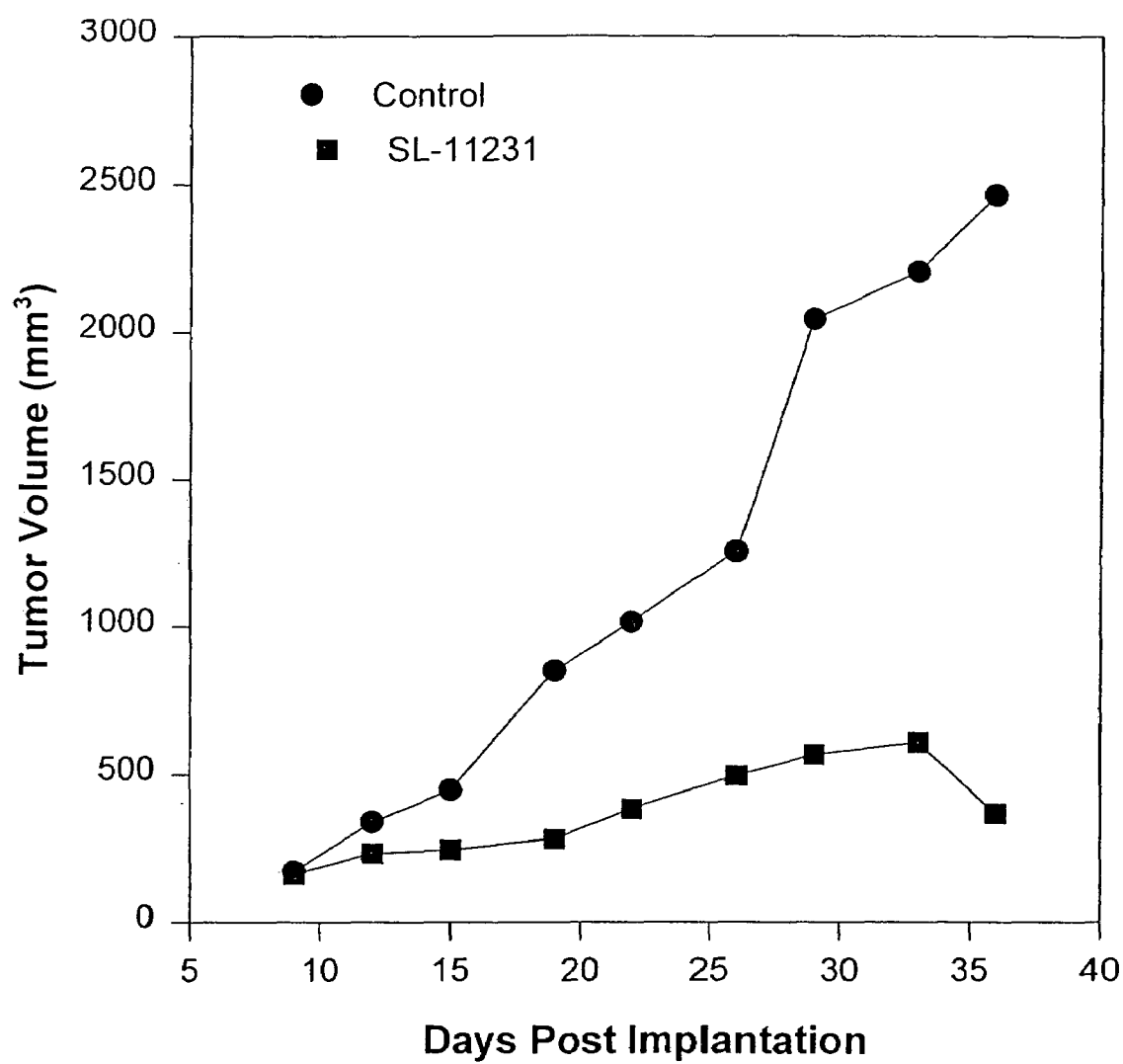
FIG. 10 is a graph depicting the effect of SL-11231 on growth of BxPC-3 human pancreatic tumor xenograft. Circles indicate data for control, squares indicate data for SL-11231.

Also, both SL-11218 and SL-11231 effectively inhibit human pancreatic tumor growth in nude mice xenograft at a dose of 50 mg/kg (FIG. 9) and 12.5 mg/kg i.p. (FIG. 10), respectively, administered i.p. q1d×5 in 2 cycles with a break of 10 days between each cycle.

Figure 11A:
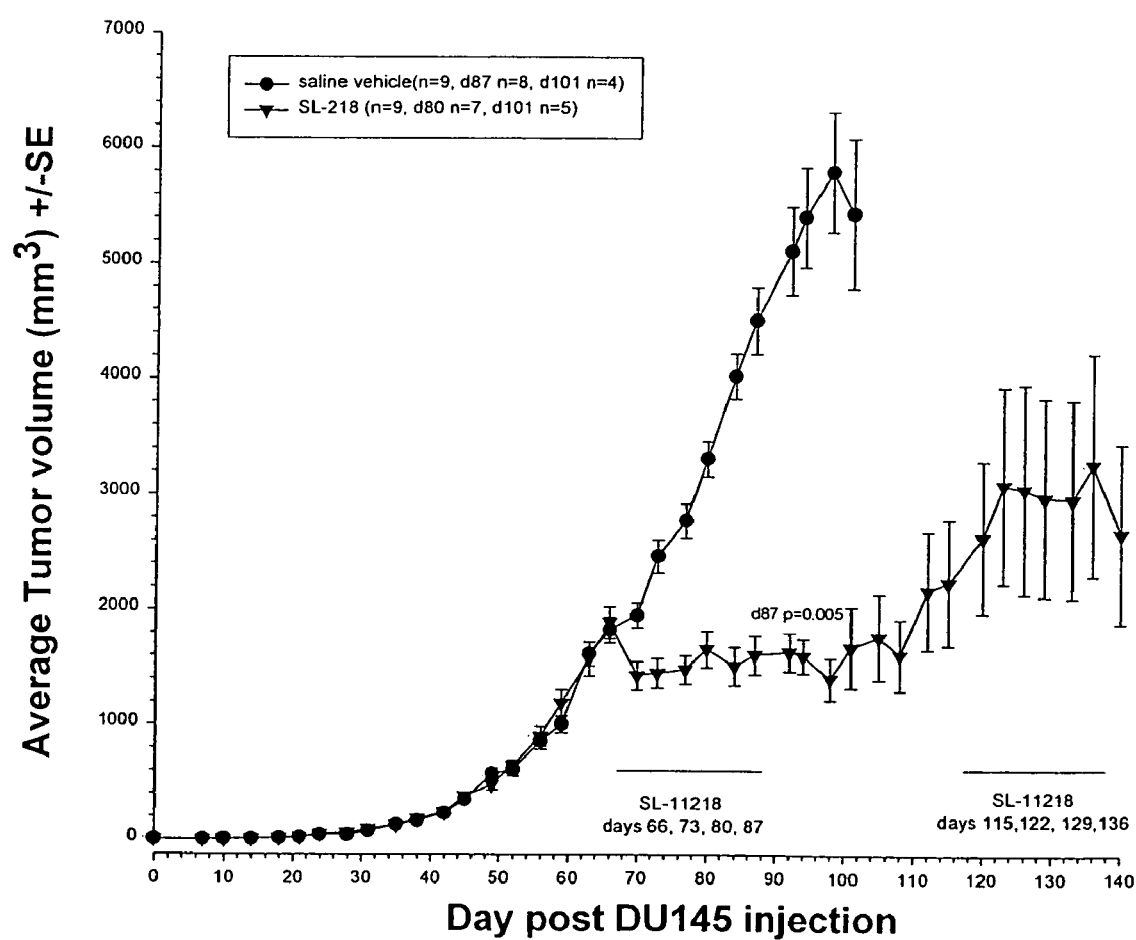
FIG. 11a is a graph depicting the efficacy of saline vs. SL-11218 against large DU145 xenografts (treatment started D66 q1w×4 for 2 cycles). Circles indicate data for control, triangles indicate data for SL-11218.
Figure 11B:
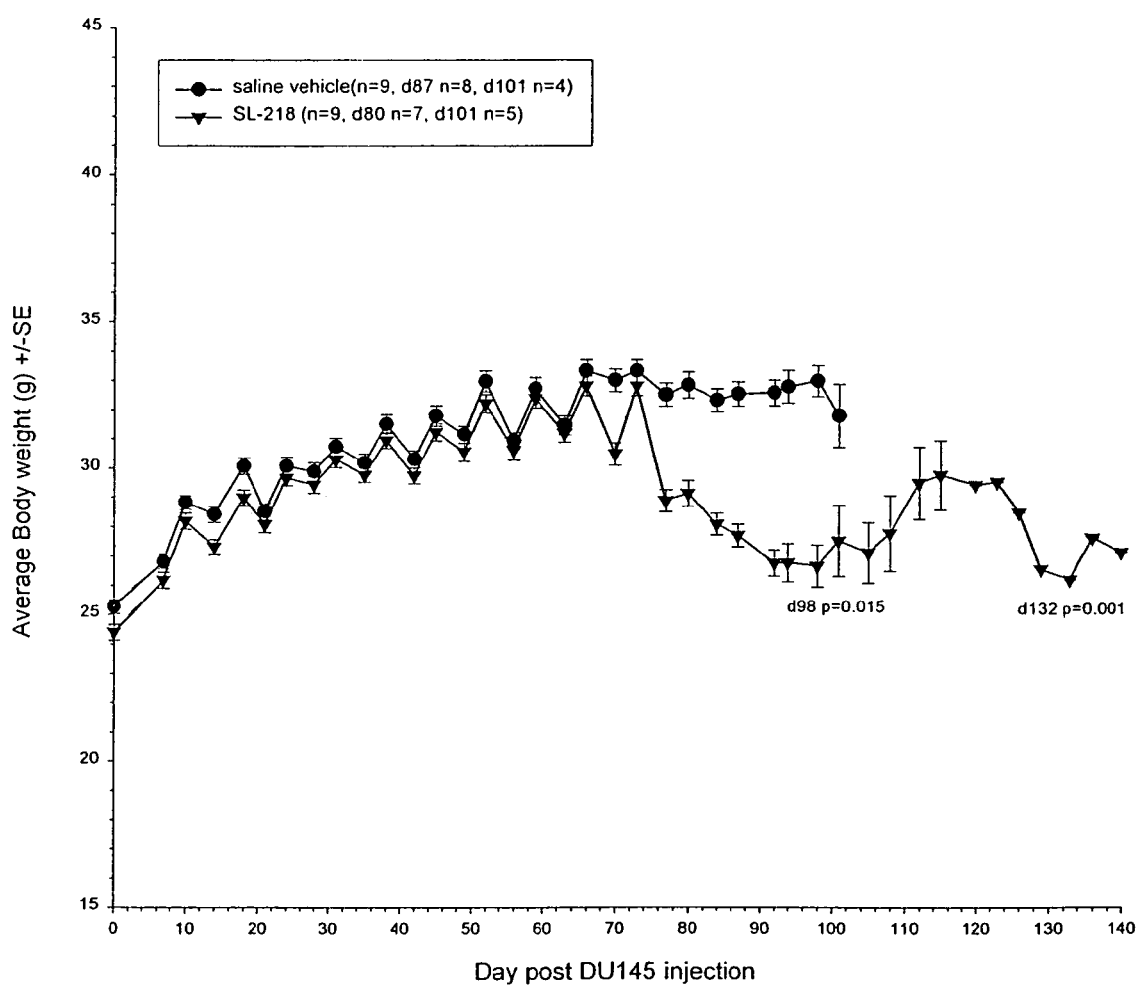
FIG. 11b is a graph depicting the effect of SL-11218 treatment on large-tumor-bearing animal body weight. Circles indicate data for control, triangles indicate data for SL-11218.

In addition, SL-11218 at a dose of 75 mg/kg i.p. for q1w×4 stabilized large (~2000 mm$^3$) DU-145 tumor xenograft for 2 cycles with a 4 week gap between each cycle (FIG. 11a). Male athymic nude mice were given s.c. injections of 1×10$^6$ DU145 cells on Day 0. Beginning on Day 10, mice were given acidified water vehicle orally at 10 ml/kg dosing volume 1× weekly for 8 weeks. On D66 mice began weekly treatment of saline versus SL-11218 i.p. After cycle 1 there was a 27% reduction in tumor volume compared to vehicle treated controls. After cycle 2 there was a significant reduction of 64% with 15% drop in body weight which recovered between cycles. (Cycle 1, administration on days 66, 73, 80, 87; cycle 2, administration on days 115, 122, 129, 136.) BW p values were compared to untreated controls. At d87, p=0.005 for SL-11218. (For saline vehicle, n=9; at d 87 n=8; at d 101, n=4; for SL-11218 n=9; d 80 n=7; d 101 n=5). FIG. 11b indicates the effect of SL-11218 on animal bodyweight (saline vehicle, n=9, at d87, n=8; at d101 n=4; for SL-11218, n=9; at d80, n=7, at d101 n=5; p=0.015 at d98 and 0.001 at d132).

All references, publications, patents and patent applications mentioned herein are hereby incorporated by reference herein in their entirety.

Although the foregoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

What is claimed is:

1. A method of making a compound of the formula:

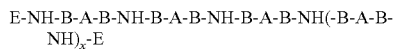

wherein A is independently selected from the group consisting of a single bond, $C_2$–$C_6$ alkyl, $C_2$–$C_6$ hydroxyalkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl;

B is independently selected from the group consisting of a single bond, $C_1$–$C_6$ alkyl, $C_1$–$C_6$ hydroxyalkyl, and $C_2$–$C_6$ alkenyl;

E is independently selected from the group consisting of H, $C_1$–$C_6$ alkyl, $C_1$–$C_6$ hydroxyalkyl, $C_2$–$C_6$ alkenyl, and $C_2$–$C_6$ alkynyl; and x is an integer from 0 to 16;

with the proviso that at least one A moiety is cyclopropyl, and that each -B-A-B- subunit contains at least two carbon atoms;

and all salts and stereoisomers thereof; comprising adding a carbene-bearing or carbene equivalent-bearing compound across a double bond of an alkene compound to form a cyclopropyl ring, wherein the carbene-bearing or carbene equivalent-bearing compound is an ylide, and wherein the carbene-bearing or carbene equivalent-bearing compound has at least one carboxylic ester and the alkene compound has at least one carboxylic ester;

converting the carboxylic esters to free carboxylic acids;

activating the free carboxylic acids with a leaving group; and reacting the activated carboxylic acids with amine-bearing compounds to form the compounds of the formula above.

2. The method of claim 1, where the compound is of the formula:

3. The method of claim 1, where the compound is of the formula:

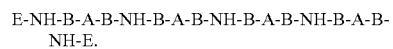

4. The method of claim 1, where the compound is of the formula:

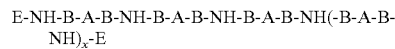

wherein x is an integer between 2 and 16.

5. The method of claim 1, wherein E is selected from H, $C_1$–$C_2$ alkyl, and t-butyl.

6. The method of claim 1, wherein E is —$CH_2CH_3$.

7. The method of claim 1, wherein each -B-A-B- subunit which does not contain a cyclopropyl moiety is independently selected from $C_2$–$C_4$ alkyl.

8. The method of claim 1, wherein each -B-A-B- subunit which does not contain a cyclopropyl moiety is —$CH_2CH_2CH_2CH_2$—.

9. The method of claim 1, wherein each -B-A-B- subunit which does not contain a cyclopropyl moiety is —$CH_2CH_2CH_2$—.

10. The method of claim 1, wherein each -B-A-B- subunit which contains a cyclopropyl moiety is

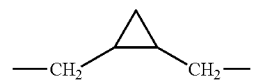

in the E configuration.

11. The method of claim 1, wherein each -B-A-B- subunit which contains a cyclopropyl moiety is

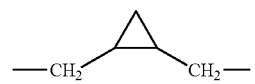

in the Z configuration.

12. The method of claim 1, further comprising reducing any amide groups formed by reacting the activated carboxylic acids with amine-bearing compounds.

13. A method of making a compound of the formula:

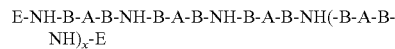

wherein A is independently selected from the group consisting of a single bond, $C_2$–$C_6$ alkyl, $C_2$–$C_6$ hydroxyalkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl;

B is independently selected from the group consisting of a single bond, $C_1$–$C_6$ alkyl, $C_1$–$C_6$ hydroxyalkyl, and $C_2$–$C_6$ alkenyl;

E is independently selected from the group consisting of H, $C_1$–$C_6$ alkyl, $C_1$–$C_6$ hydroxyalkyl, $C_2$–$C_6$ alkenyl, and $C_2$–$C_6$ alkynyl; and x is an integer from 0 to 16;

with the proviso that at least one A moiety is cyclopropyl, and that each -B-A-B- subunit contains at least two carbon atoms;

and all salts and stereoisomers thereof; comprising adding a carbene-bearing or carbene equivalent-bearing compound across a double bond of an alkene compound to form a cyclopropyl ring, wherein the carbene-bearing or carbene equivalent-bearing compound is an ylide, and wherein the carbene-bearing or carbene equivalent-bearing compound has at least one carboxylic ester and the alkene compound has at least one carboxylic ester;

reducing the carboxylic esters to alcohols;

converting the alcohols to leaving groups and reacting the converted groups with amine-bearing compounds to form the compounds of the formula above.

14. The method of claim 13, where the compound is of the formula:

E-NH-B-A-B-NH-B-A-B-NH-B-A-B-NH-E.

15. The method of claim 13, where the compound is of the formula:

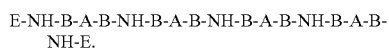

E-NH-B-A-B-NH-B-A-B-NH-B-A-B-NH-B-A-B-NH-E.

16. The method of claim 13, where the compound is of the formula:

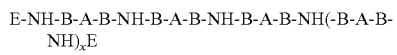

E-NH-B-A-B-NH-B-A-B-NH-B-A-B-NH(-B-A-B-NH)$_x$E wherein x is an integer between 2 and 16.

17. The method of claim 13, wherein E is selected from H, $C_1$–$C_2$ alkyl, and t-butyl.

18. The method of claim 13, wherein E is —$CH_2CH_3$.

19. The method of claim 13, wherein each -B-A-B- subunit which does not contain a cyclopropyl moiety is independently selected from $C_2$–$C_4$ alkyl.

20. The method of claim 13, wherein each -B-A-B- subunit which does not contain a cyclopropyl moiety is —$CH_2CH_2CH_2CH_2$—.

21. The method of claim 13, wherein each -B-A-B- subunit which does not contain a cyclopropyl moiety is —$CH_2CH_2CH_2$—.

22. The method of claim 13, wherein each -B-A-B- subunit which contains a cyclopropyl moiety is

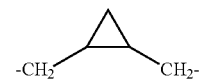

in the E configuration.

23. The method of claim 13, wherein each -B-A-B- subunit which contains a cyclopropyl moiety is

in the Z configuration.

24. The method of claim 1, wherein the alkene compound is ethyl acrylate.

25. The method of claim 1, wherein the ylide is a sulfur ylide.

26. The method of claim 1, wherein the step of activating the carboxylic acids with a leaving group consists of reacting the carboxylic acids with thionyl chloride to produce carboxylic acid chlorides.

* * * * *